(12) United States Patent
Kassab

(10) Patent No.: US 9,872,759 B2
(45) Date of Patent: Jan. 23, 2018

(54) DEVICES AND METHODS FOR ASSISTING VALVE FUNCTION, REPLACING VENOUS VALVES, AND PREDICTING VALVE TREATMENT SUCCESS

(71) Applicant: 3DT Holdings, LLC, San Diego, CA (US)

(72) Inventor: Ghassan S. Kassab, La Jolla, CA (US)

(73) Assignee: 3DT Holdings, LLC, San Diego, CA (US)

( * ) Notice: Subject to any disclaimer, the term of this patent is extended or adjusted under 35 U.S.C. 154(b) by 214 days.

(21) Appl. No.: 14/345,252

(22) PCT Filed: Sep. 17, 2012

(86) PCT No.: PCT/US2012/055752
§ 371 (c)(1),
(2) Date: Mar. 16, 2014

(87) PCT Pub. No.: WO2013/040554
PCT Pub. Date: Mar. 21, 2013

(65) Prior Publication Data
US 2015/0039079 A1    Feb. 5, 2015

Related U.S. Application Data

(60) Provisional application No. 61/547,378, filed on Oct. 14, 2011, provisional application No. 61/535,689, filed on Sep. 16, 2011.

(51) Int. Cl.
*A61F 2/06* (2013.01)
*A61B 17/12* (2006.01)
(Continued)

(52) U.S. Cl.
CPC .......... *A61F 2/06* (2013.01); *A61B 17/12013* (2013.01); *A61F 2/2475* (2013.01);
(Continued)

(58) Field of Classification Search
CPC .... A61F 2/2412; A61F 2/2418; A61F 2/2469; A61F 2/2475; A61F 2/24
See application file for complete search history.

(56) References Cited

U.S. PATENT DOCUMENTS 5,509,888 A    4/1996  Miller
6,077,227 A    6/2000  Miesel et al.
(Continued)

OTHER PUBLICATIONS

International Searching Authority, International Search Report, PCT/US2012/055752, dated Feb. 25, 2013.
(Continued)

*Primary Examiner* — Jason-Dennis Stewart
(74) *Attorney, Agent, or Firm* — Reichel Stohry LLP; Mark C. Reichel; Natalie J. Dean

(57) ABSTRACT

Devices and methods for assisting valve function, replacing venous valves, and predicting valve treatment successes. In at least one exemplary embodiment of an endograft body configured for expansion within a luminal organ of the present disclosure, the endograft body comprises (a) a first portion having a proximal end defining a proximal end aperture and a distal end defining a distal end aperture, the first portion configured to increase a velocity of fluid flowing therethrough, (b) a second portion having a second portion proximal end defining a second portion proximal end aperture and a second portion distal end defining a second portion distal end aperture.

20 Claims, 14 Drawing Sheets

(51) Int. Cl.
  *A61F 2/24* (2006.01)
  *A61B 17/00* (2006.01)
(52) U.S. Cl.
  CPC ... *A61B 2017/00557* (2013.01); *A61F 2/2433* (2013.01); *A61F 2002/068* (2013.01); *A61F 2240/002* (2013.01)

(56) References Cited

U.S. PATENT DOCUMENTS

| | | |
|---|---|---|
| 6,682,558 B2 | 1/2004 | Tu et al. |
| 2003/0023303 A1 | 1/2003 | Palmaz |
| 2004/0147803 A1 | 7/2004 | Hegde et al. |
| 2006/0206192 A1 | 9/2006 | Tower et al. |
| 2007/0014452 A1* | 1/2007 | Suresh et al. .............. 382/128 |
| 2007/0213813 A1* | 9/2007 | Von Segesser et al. ..... 623/2.18 |
| 2007/0255394 A1 | 11/2007 | Ryan |
| 2007/0260327 A1 | 11/2007 | Case et al. |
| 2009/0171435 A1 | 7/2009 | Kuppurathanam et al. |
| 2010/0210957 A1 | 8/2010 | Inoue |
| 2011/0087337 A1* | 4/2011 | Forsell ...................... 623/23.68 |
| 2011/0153286 A1 | 6/2011 | Zauener et al. |
| 2011/0160836 A1 | 6/2011 | Behan |

OTHER PUBLICATIONS

International Searching Authority (ISA), Written Opinion of the ISA, PCT/US2012/055752, dated Feb. 25, 2013.

\* cited by examiner

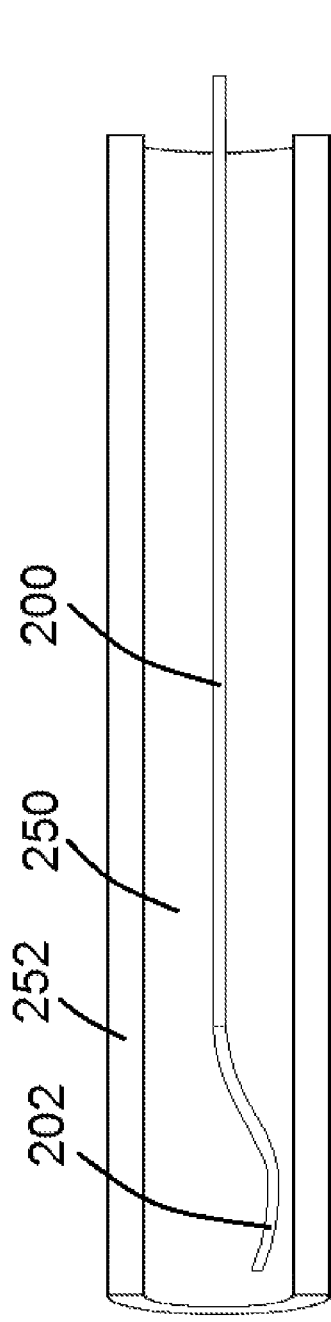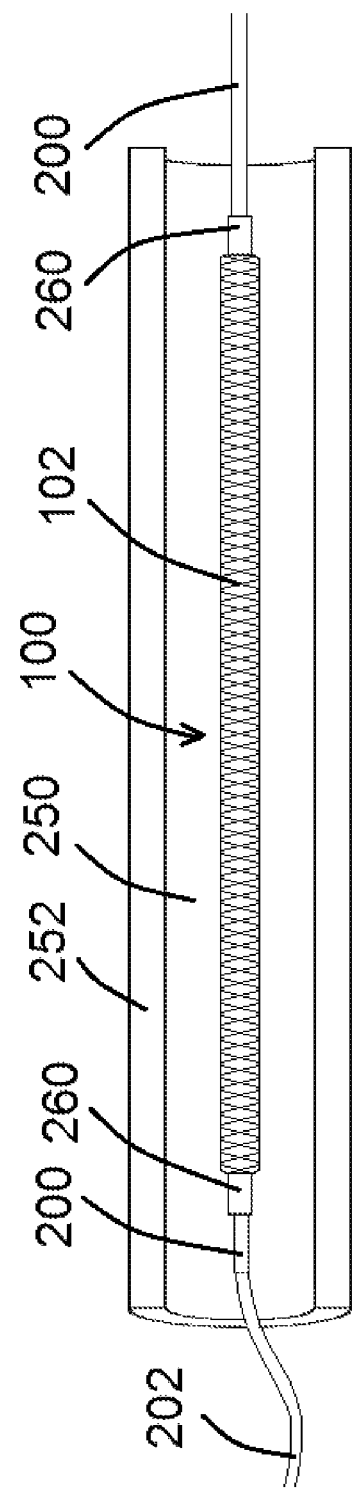

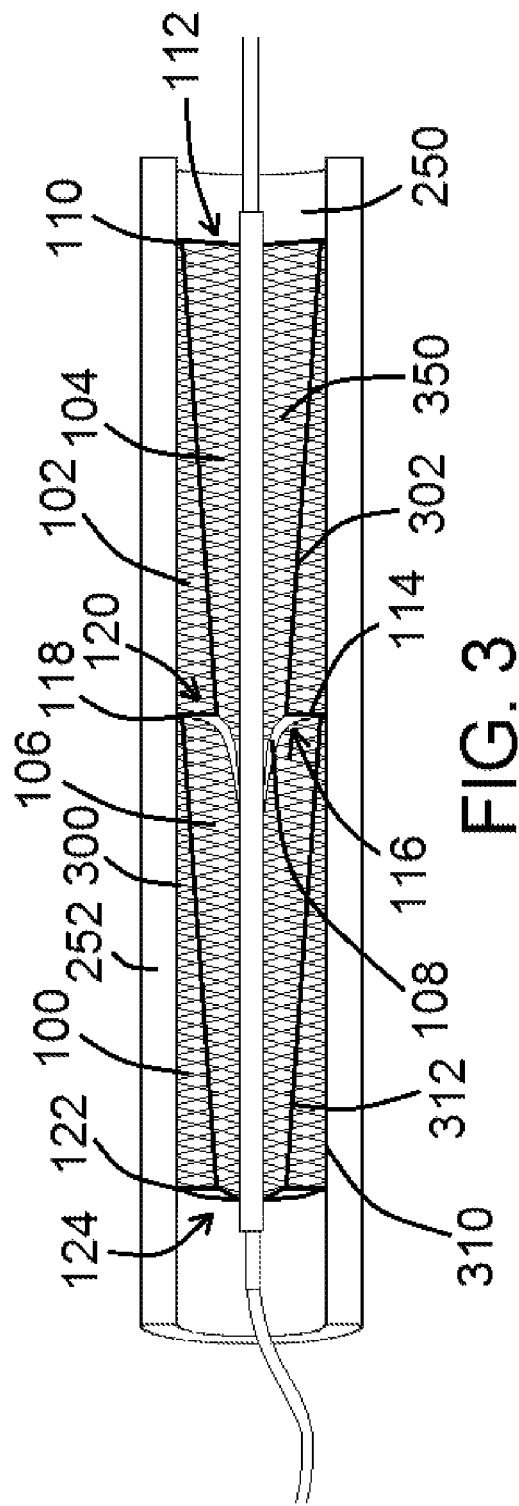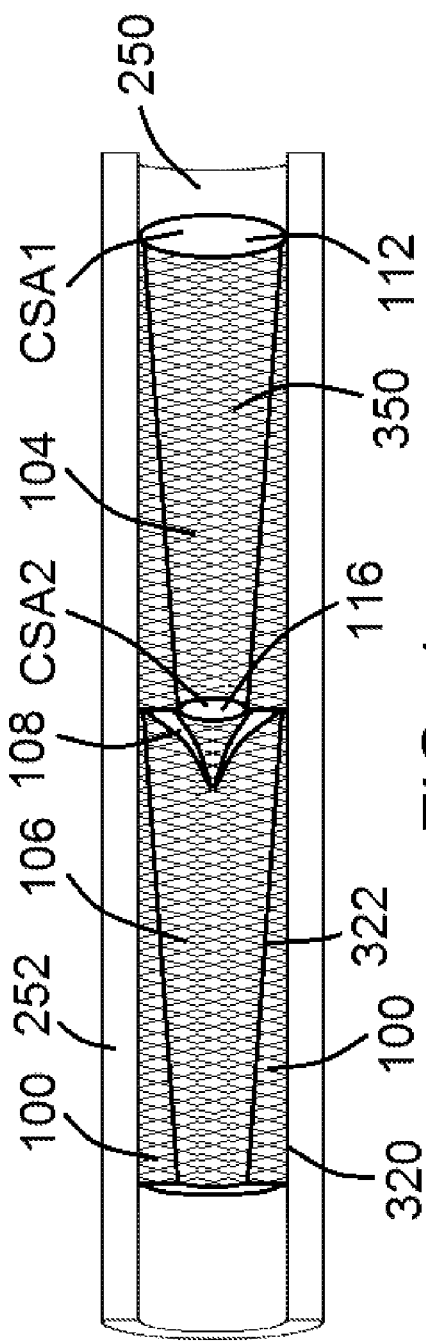

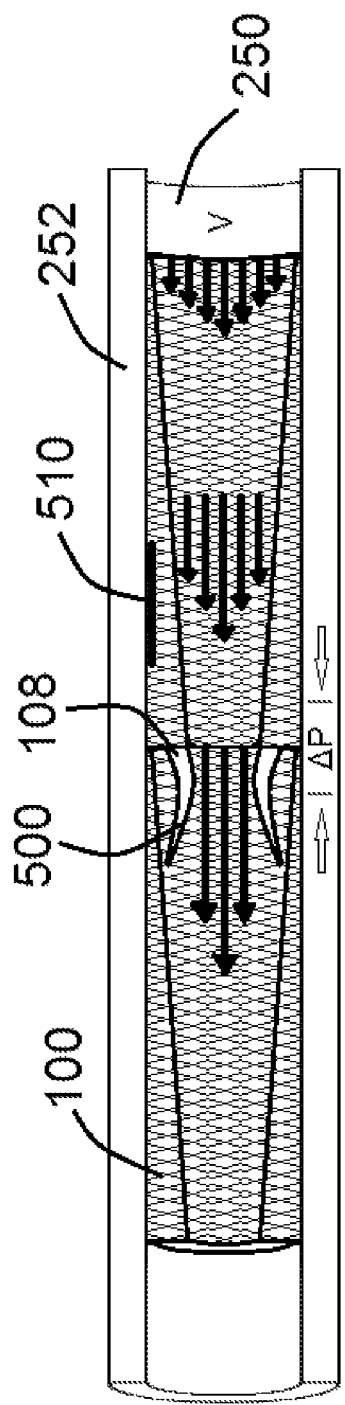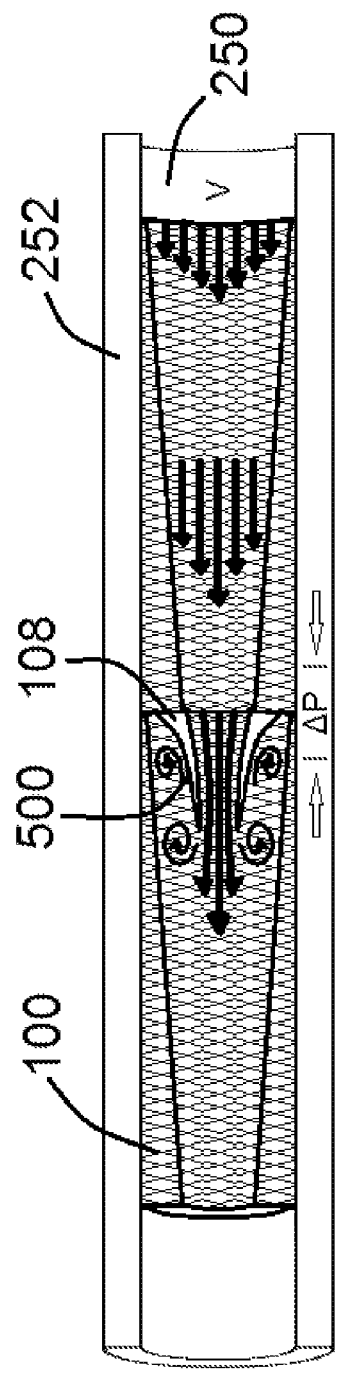

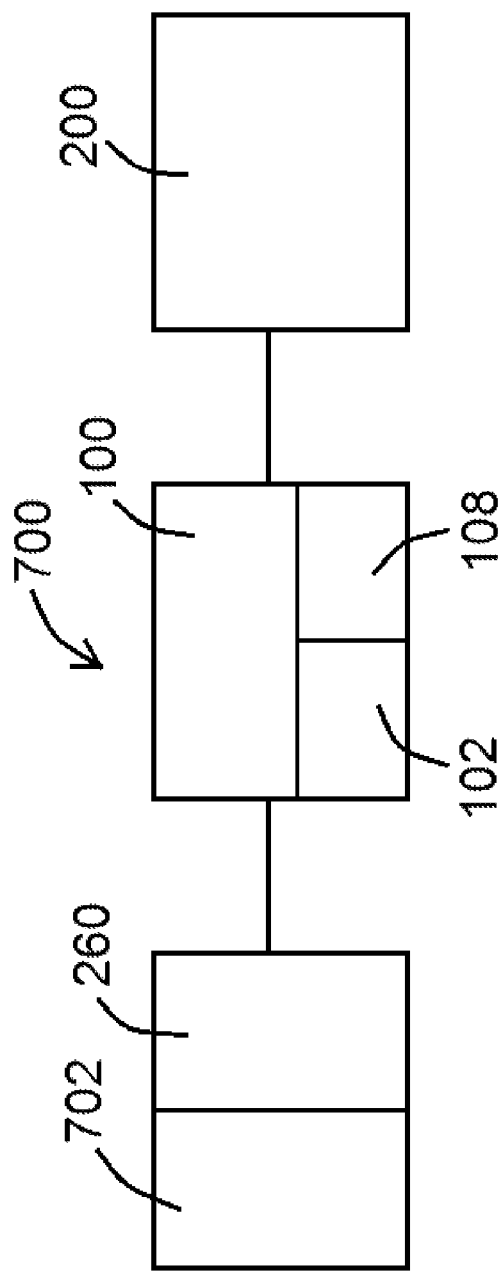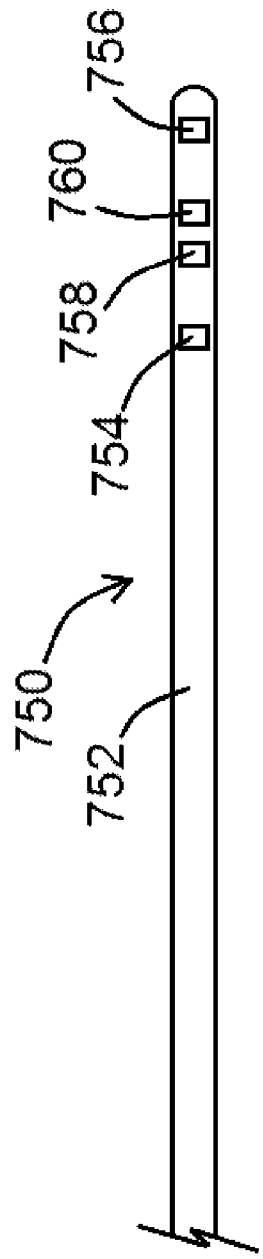

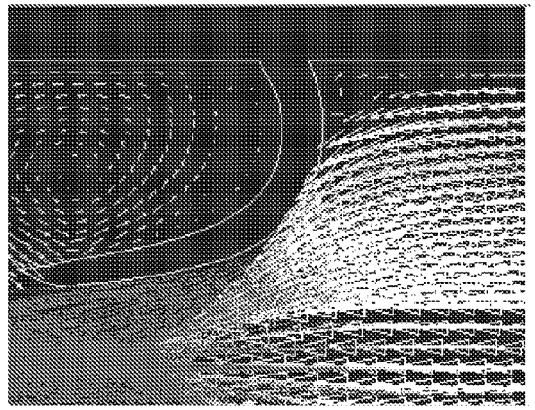 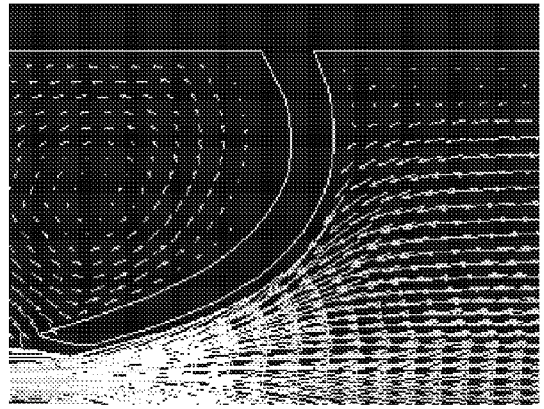
FIG. 14A    FIG. 14B
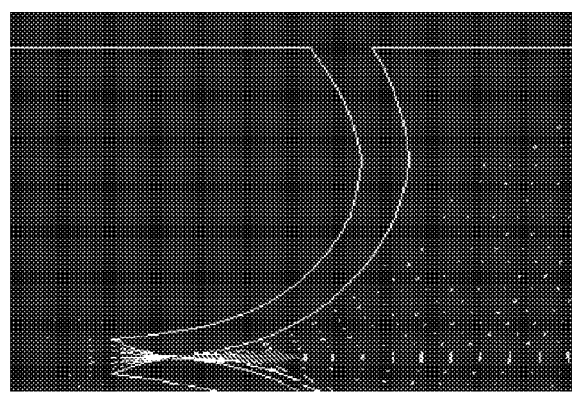
FIG. 14C

DEVICES AND METHODS FOR ASSISTING VALVE FUNCTION, REPLACING VENOUS VALVES, AND PREDICTING VALVE TREATMENT SUCCESS

PRIORITY

The present application is related to, and claims the priority benefit of, International Patent Application Serial No. PCT/US12/55752, filed Sep. 17, 2012, which is related to, and claims the priority benefit of, U.S. Provisional Patent Application Ser. No. 61/535,689, filed Sep. 16, 2011, and U.S. Provisional Patent Application Ser. No. 61/547,378, filed Oct. 14, 2011. The contents of each of these applications are incorporated by reference in their entirety into this disclosure.

BACKGROUND

It has been known for several years that the three contributing factors to venous thrombosis are stasis (slow blood flow), changes in blood composition, and changes in vessel wall. These three contributing factors are known as Virchow's triad.

Venous insufficiency is a complex disease that involves thrombosis (blood clot abnormalities and/or endothelial dysfunction), venous hypertension, reverse flow (reflux), and venous remodeling, amongst others. The two major contributors to venous insufficiency are venous occlusion and valve incompetence (reflux).

Blood stasis promotes a thrombogenic response through various biochemical activators. Attempts have been made to create percutaneous venous valve stent systems to replace a prolapsed or otherwise dysfunctional venous valve, but no attempt has previously been proven successful. In order for such a system to work, one of the contributing factors to venous blood thrombosis, namely stasis, must be overcome in order for the valve to remain patent and to avoid thrombosis/clotting A valve device or system, operable to replace a prolapsed or otherwise dysfunctional venous valve that effectively operates and overcomes the stasis contributing factor, would be well-received in the marketplace. In addition, a device useful to assist blood flow through a blood vessel, methods of using the same, and methods for predicting a potential success for an individual patient in connection with a potential valve treatment procedure, would also be well-received in the marketplace.

BRIEF SUMMARY

In at least one exemplary embodiment of an endograft body configured for expansion within a luminal organ of the present disclosure, the endograft body comprises a first portion having a proximal end defining a proximal end aperture and a distal end defining a distal end aperture, the first portion configured to increase a velocity of fluid flowing therethrough, a second portion having a second portion proximal end defining a second portion proximal end aperture and a second portion distal end defining a second portion distal end aperture, wherein the distal end of the first portion is adjacent to the second portion proximal end, and a valve portion positioned at or near the second portion proximal end, the valve portion configured to receive the fluid flowing through the distal end aperture of the first portion. In another embodiment, the first portion tapers toward the distal end so that the distal end aperture has a relatively smaller cross-sectional area than the proximal end aperture when the endograft body is expanded. In yet another embodiment, the second portion tapers toward the second portion distal end so that the second portion distal end aperture has a relatively smaller cross-sectional area than the second portion proximal end aperture when the endograft body is expanded. In an additional embodiment, the second portion tapers toward the second portion distal end so that the second portion distal end aperture has a relatively smaller cross-sectional area than the second portion proximal end aperture when the endograft body is expanded.

In at least one exemplary embodiment of an endograft body configured for expansion within a luminal organ of the present disclosure, the second portion is configured to increase the velocity of fluid flowing therethrough. In an additional embodiment, the endograft body is configured to expand from a collapsed configuration to an expanded configuration. In yet an additional embodiment, the endograft body has a first configuration, the first configuration sized so that the endograft body may fit within the luminal organ. In another embodiment, the endograft body has a first configuration, the first configuration sized so that the endograft body can be delivered within the luminal organ.

In at least one exemplary embodiment of an endograft body configured for expansion within a luminal organ of the present disclosure, the endograft has a second configuration, the second configuration sized so that the endograft body may be securely positioned within the luminal organ upon expansion. In another embodiment, the valve portion is coupled to the first portion. In yet another embodiment, the valve portion is coupled to the second portion. In an additional embodiment, the endograft body is sized and shaped to fit around a guidewire. In at least one exemplary embodiment of an endograft body configured for expansion within a luminal organ of the present disclosure, the endograft body is sized and shaped to fit around a catheter. In an additional embodiment, the endograft body is configured for expansion due to inflation of a balloon coupled to the catheter.

In at least one exemplary embodiment of an endograft body configured for expansion within a luminal organ of the present disclosure, when the endograft body is expanded within the luminal organ, an outer portion of the endograft body contacts the luminal organ, and an inner portion of the endograft body is configured to permit fluid to flow therethrough. In an additional embodiment, the outer portion defines an outer portion wall, and wherein the inner portion defines an inner portion wall. In yet an additional embodiment, the outer portion defines an outer portion relative surface, and wherein the inner portion defines an inner portion relative surface. In another embodiment, the first portion is configured to increase the velocity of the fluid flowing therethrough when the endograft body is expanded within the luminal organ.

In at least one exemplary embodiment of an endograft body configured for expansion within a luminal organ of the present disclosure, the second portion is configured to increase the velocity of the fluid flowing therethrough when the endograft body is expanded within the luminal organ. In another embodiment, when the endograft body is expanded within the luminal organ, fluid flowing through the first portion increases in velocity as the fluid approaches the valve portion. In yet another embodiment, when the endograft body is expanded within the luminal organ, fluid flowing through the first portion increases in velocity as the fluid approaches the valve portion and increases shear stresses at the valve portion. In an additional embodiment, when the endograft body is expanded within the luminal organ, fluid flowing through the second portion increases in velocity as the fluid travels from the second portion proximal end to the second portion distal end.

In at least one exemplary embodiment of an endograft body configured for expansion within a luminal organ of the present disclosure, when the endograft body is expanded within the luminal organ, fluid flowing through the second portion increases in velocity as the fluid travels from the second portion proximal end to the second portion distal end. In an additional embodiment, the endograft body is configured for introduction into the luminal organ along a guidewire positioned within at least part of the luminal organ. In yet an additional embodiment, the endograft body is further configured for expansion within the luminal organ while positioned along the guidewire. In another embodiment, the endograft valve device is configured as a venous endograft valve device and is further configured to fit within a vein. In yet another embodiment, the endograft valve device is sized and shaped to fit within the luminal organ, the size and shape based upon data obtained relative to a patient's venous geometry at a first location.

In at least one exemplary embodiment of an endograft body configured for expansion within a luminal organ of the present disclosure, the endograft valve device is selected from a group of potential endograft valve devices based upon data obtained relative to a patient's venous geometry at a first location. In another embodiment, the valve of the endograft valve device is sized and shaped based upon data obtained relative to a patient's venous geometry at a first location. In yet another embodiment, the valve of the endograft valve device is selected from a group of potential valves based upon data obtained relative to a patient's venous geometry at a first location. In an additional embodiment, the endograft valve device is sized and shaped to fit within the luminal organ, the size and shape based upon data obtained relative to a flow velocity of blood within a vein of a patient.

In at least one exemplary embodiment of an endograft body configured for expansion within a luminal organ of the present disclosure, the endograft valve device is selected from a group of potential endograft valve devices based upon data obtained relative to a flow velocity of blood within a vein of a patient. In an additional embodiment, the valve of the endograft valve device is sized and shaped based upon data obtained relative to a flow velocity of blood within a vein of a patient. In yet an additional embodiment, the valve of the endograft valve device is selected from a group of potential valves based upon data obtained relative to a flow velocity of blood within a vein of a patient. In another embodiment, the endograft valve device is sized and shaped to fit within the luminal organ, the size and shape based upon additional data obtained relative to a flow velocity of blood within a vein of the patient at or near the first location. In yet another embodiment, the endograft valve device is selected from a group of potential endograft valve devices based upon additional data obtained relative to a flow velocity of blood within a vein of the patient at or near the first location.

In at least one exemplary embodiment of an endograft body configured for expansion within a luminal organ of the present disclosure, the valve of the endograft valve device is sized and shaped based upon additional data obtained relative to a flow velocity of blood within a vein of the patient at or near the first location. In another embodiment, the valve of the endograft valve device is selected from a group of potential valves based upon additional data obtained relative to a flow velocity of blood within a vein of the patient at or near the first location. In yet another embodiment, the endograft valve device is configured based upon a digital model of a luminal organ of a patient. In an additional embodiment, the digital model incorporates a valve input indicative of at least one digital valve device. In yet an additional embodiment, the at least one digital valve device includes a configuration of the endograft valve device.

In at least one exemplary embodiment of an endograft body configured for expansion within a luminal organ of the present disclosure, the at least one digital valve device includes a plurality of other digital valve devices in addition to a configuration of the endograft valve device. In an additional embodiment, the digital incorporates a vessel geometry input indicative of data obtained relative to a patient's venous geometry at a first location. In yet an additional embodiment, the digital model incorporates a flow velocity input indicative of data obtained relative to a flow velocity of blood within the vein of the patient.

In at least one exemplary embodiment of an endograft body configured for expansion within a luminal organ of the present disclosure, the digital model further incorporates a flow velocity input indicative of data obtained relative to a flow velocity of blood within the vein of the patient. In another embodiment, the digital model is configured to generate at least one model output based upon at least the vessel geometry input and the flow velocity input. In yet another embodiment, the at least one model output indicates whether or not the patient is suitable for a valve procedure. In an additional embodiment, the digital model further incorporates a valve input indicative of at least one digital valve device. In yet an additional embodiment, the digital model is configured to generate at least one model output based upon at least the vessel geometry input, the flow velocity input, and the valve input.

In at least one exemplary embodiment of an endograft body configured for expansion within a luminal organ of the present disclosure, the at least one model output indicates whether or not the patient is suitable for a valve procedure based on one or more characteristics of the valve input. In an additional embodiment, the one or more characteristics of the valve input is/are selected from the group consisting of a wall stress characteristic, a wall shear stress characteristic, a gradient of wall shear stress characteristic, an oscillatory shear index characteristic, and a leaflet characteristic. In yet an additional embodiment, the at least one model output indicates that the patient is suitable for a valve procedure based upon at least the vessel geometry input, the flow velocity input, and the valve input, as compared to at least one threshold parameter. In another embodiment, the at least one threshold parameter is selected from the group consisting of a minimum vessel diameter, a vessel diameter range, a minimum flow velocity, a flow velocity range, a minimum vessel cross-sectional area, a vessel cross-sectional area range, a minimum wall stress parameter, a maximum wall stress parameter, a minimum wall shear stress parameter, a maximum wall shear stress parameter, a minimum gradient of wall shear stress parameter, a maximum gradient of wall shear stress parameter, a minimum oscillatory shear index parameter, a maximum oscillatory shear index parameter, and a leaflet closure parameter.

In at least one exemplary embodiment of an endograft body configured for expansion within a luminal organ of the present disclosure, the at least one threshold parameter is selected from the group consisting of a vessel diameter larger than or approximately 8 mm, a cross-sectional area larger than or approximately 0.5 cm$^2$, a flow velocity greater than or approximately 30 ml/min, and a wall shear stress greater than or approximately 5 dynes/cm$^2$ and less than or approximately 10 dynes/cm$^2$. In another embodiment, the at least one model output indicates that the patient is not suitable for a valve procedure based upon fibrosis within the patient's vessel geometry. In yet another embodiment, the at least one model output indicates that the patient is not suitable for a valve procedure based upon at least the vessel geometry input, the flow velocity input, and the valve input, as compared to at least one threshold parameter. In an additional embodiment, the at least one threshold parameter is selected from the group consisting of a vessel diameter less than or approximately 8 mm, a cross-sectional area less than or approximately 0.5 cm$^2$, a flow velocity less than or approximately 30 ml/min, a flow velocity greater than or approximately 150 ml/min, a wall shear stress less than or approximately 5 dynes/cm$^2$, and a wall shear stress greater than or approximately 10 dynes/cm$^2$.

In at least one exemplary embodiment of an endograft body configured for expansion within a luminal organ of the present disclosure, the at least one digital valve device includes a configuration of the endograft valve device, and the endograft valve device is selected for implantation into the patient based upon the model output. In an additional embodiment, the data obtained relative to a patient's venous geometry at a first location is obtained using a detection device selected from the group consisting of a duplex ultrasound device, a computed tomography device, and a magnetic resonance imaging device. In yet an additional embodiment, the data obtained relative to a flow velocity of blood within the vein of the patient is obtained using a detection device selected from the group consisting of a duplex ultrasound device, a computed tomography device, and a magnetic resonance imaging device. In another embodiment, the data obtained relative to a patient's venous geometry at a first location is obtained using an impedance device selected from the group consisting of an impedance wire and an impedance catheter. In yet another embodiment, the data obtained relative to a patient's venous geometry at a first location is obtained using an impedance device selected from the group consisting of an impedance wire and an impedance catheter, each of the impedance wire and the impedance catheter comprising a device body and at least four electrodes positioned thereon, the at least four electrodes comprising two electrodes configured to excite an electric field and two electrodes configured to obtain a conductance measurement within the electric field.

In at least one exemplary embodiment of an endograft body configured for expansion within a luminal organ of the present disclosure, the endograft valve device is configured based upon a first digital model having a vessel geometry input indicative of data obtained relative to a patient's venous geometry at a first location incorporated therein. In another embodiment, the endograft valve device is further configured based upon a second digital model having a flow velocity input indicative of data obtained relative to a flow velocity of blood within a vein of the patient at or near the first location incorporated therein. In yet another embodiment, the first digital model and the second digital model produce patient venous data. In an additional embodiment, one or both of the first digital model and the second digital model incorporate a valve input indicative of at least one digital valve device therein, the at least one digital valve device including a configuration of the endograft valve device. In yet an additional embodiment, the endograft valve device is selected for implantation into the patient based upon the venous data and the digital model of at least one digital valve device.

In at least one exemplary embodiment of an endograft body configured for expansion within a luminal organ of the present disclosure, the endograft valve device is selected for implantation into the patient also based upon shear stress data from one or both of the first digital model and the second digital model. In an additional embodiment, the valve portion comprises leaflets. In yet an additional embodiment, the endograft valve device further comprises an agent selected from the group consisting of an anti-clotting agent and an anti-inflammatory agent, the agent positioned upon at least a portion of the endograft valve device. In another embodiment, the agent is positioned upon at least an inner portion of the endograft valve device. In yet another embodiment, the agent is positioned upon at least an outer portion of the endograft valve device.

In at least one exemplary embodiment of an endograft body configured for expansion within a luminal organ of the present disclosure, the agent is selected from the group consisting of heparin, thrombomodulin, endothelial cell protein C, another anti-clotting drug, protease inhibitor(s), $\alpha$1-antitrypsin, $\alpha$1-macroglobulin, $\alpha$1-antichymotrypsin, and another anti-inflammatory drug. In another embodiment, the endograft body is comprises of a biologically-compatible material selected from the group consisting of polytetrafluoroethylene, Gore-Tex®, and nitinol. In yet another embodiment, the endograft valve device comprises a component of a valve system, the valve system further comprising a guidewire and a catheter, wherein the catheter is configured to fit around the guidewire, and wherein the endograft valve device is configured to fit around the catheter. In an additional embodiment, the catheter comprises a balloon catheter.

In at least one exemplary embodiment of an endograft body configured for expansion within a luminal organ of the present disclosure, the endograft valve device comprises a component of a valve system, the valve system further comprising a cuff configured to fit around a blood vessel and further configured to periodically compress the blood vessel. In an additional embodiment, the valve system further comprises a processor operably coupled to the cuff, the processor configured to control a compression rate and a relaxation rate. In yet an additional embodiment, when the cuff is positioned around the blood vessel at a second location, operation of the processor causes the cuff to compress the blood vessel and relax compression of the blood vessel, whereby relaxation at the relaxation rate increases a rate of blood flow through the blood vessel at the second location. In another embodiment, the compression rate is slower than the relaxation rate. In yet another embodiment, the valve system further comprises a power source operably coupled to the cuff, the power source configured to provide power to the cuff and/or the processor to facilitate compression and relaxation of the cuff.

In at least one exemplary embodiment of an endograft body configured for expansion within a luminal organ of the present disclosure, the valve system further comprises a connector coupled to the power source and to the cuff, the connector configured to allow power from the power source to be transmitted therethrough to the cuff. In another embodiment, the connector comprises a wire. In yet another embodiment, the processor is configured so that the compression rate and the relaxation rate can be changed to a different compression rate and a different relaxation rate. In an additional embodiment, when the endograft valve device is positioned within the blood vessel at a first location and wherein when the cuff is positioned around the blood vessel at the second location, operation of the cuff increases the rate of blood flow through the blood vessel at the first location and the second location. In yet an additional embodiment, the first location is proximal to the second location relative to a direction of blood flow, and wherein operation of the cuff increases the rate of blood flow through the blood vessel at the first location by effectively pulling blood through the endograft valve device.

In at least one exemplary embodiment of an endograft body configured for expansion within a luminal organ of the present disclosure, the first location is distal to the second location relative to a direction of blood flow, and wherein operation of the cuff increases the rate of blood flow through the blood vessel at the first location by effectively pushing blood through the endograft valve device. In another embodiment, when the cuff is positioned around the blood vessel at the second location, blood flows through the blood vessel at the second location a first rate without operation of the cuff, and the blood flows through the blood vessel at the second location at a second rate during operation of the cuff, wherein the second rate is faster than the first rate. In yet another embodiment, when the cuff is positioned around the blood vessel at the second location, blood flows through the blood vessel at the second location a first rate range without operation of the cuff, and the blood flows through the blood vessel at the second location at a second rate range during operation of the cuff, wherein the second rate range has a faster top rate than the first rate range. In an additional embodiment, when the cuff is positioned around the blood vessel at the second location, operation of the cuff increases the rate of blood flow through the blood vessel at the second location. In yet an additional embodiment, when the cuff is positioned around the blood vessel at the second location, relaxation of compression of the cuff causes blood to flow through the blood vessel at a faster rate than a native blood flow rate.

In at least one exemplary embodiment of an endograft body configured for expansion within a luminal organ of the present disclosure, when the cuff is positioned around the blood vessel at the second location, alternatively compressing the blood vessel at a first, faster rate and relaxing compression of the blood vessel at a second, slower rate facilitates blood flow through the blood vessel at the second location. In an additional embodiment, the first portion of the endograft body is configured to increase wall shear stress at the distal end relative to the proximal end. In yet an additional embodiment, when the distal end aperture has a cross-sectional area of at least half of a cross-sectional area of the proximal end aperture, wall shear stress at the distal end increases by at least 2.8 times. In another embodiment, when the endograft valve device is positioned within a blood vessel, the second portion is configured to ensure blood flow recirculation of blood flowing therethrough.

In at least one exemplary embodiment of an endograft body configured for expansion within a luminal organ of the present disclosure, when the endograft valve device is positioned within a blood vessel, the second portion is configured to establish a negative pressure drop to close the valve after the valve has opened due to blood flow therethrough. In another embodiment, the digital model comprises a processor operably coupled to a storage medium, the processor operable to generate the at least one model output, and the storage medium configured to store data relating to the vessel geometry input, the flow velocity input, the valve input, and the at least one model output.

In at least one exemplary embodiment of an endograft body configured for expansion within a luminal organ of the present disclosure, the one or more relationships are further selected from the group consisting of a mass relationship, a momentum relationship, an equilibrium equation, a strain energy function, an equilibrium condition, a kinematic condition, a dynamic condition, a multi-body interaction, a blood rheology equation, and a thrombosis kinetics equation. In another embodiment, the endograft body is stentless. In yet another embodiment, the digital model further incorporates a thrombosis input indicative of a level of thrombosis within the vessel geometry. In an additional embodiment, the digital model is configured to generate at least one model output based upon at least the vessel geometry input, the flow velocity input, the valve input, and the thrombosis input.

In at least one exemplary embodiment of an endograft body configured for expansion within a luminal organ of the present disclosure, the digital model further incorporates a rheology input indicative of a blood rheology property. In an additional embodiment, the digital model is configured to generate at least one model output based upon at least the vessel geometry input, the flow velocity input, the valve input, the thrombosis input, and the rheology input. In yet an additional embodiment, the digital model comprises a processor operably coupled to a storage medium, the processor operable to generate the at least one model output based upon one or more of the vessel geometry input, the flow velocity input, the valve input, the thrombosis input, and the rheology input, and the storage medium configured to store data relating to one or more of the vessel geometry input, the flow velocity input, the valve input, the thrombosis input, and the rheology input.

In at least one exemplary embodiment of a valve system of the present disclosure, the valve system comprises an endograft valve device, comprising an endograft body configured for expansion within a luminal organ, the endograft body comprising a first portion having a proximal end defining a proximal end aperture and a distal end defining a distal end aperture, the first portion configured to increase a velocity of fluid flowing therethrough, a second portion having a second portion proximal end defining a second portion proximal end aperture and a second portion distal end defining a second portion distal end aperture, wherein the distal end of the first portion is adjacent to the second portion proximal end, and a valve portion positioned at or near the second portion proximal end, the valve portion configured to receive the fluid flowing through the distal end aperture of the first portion; a guidewire; and a catheter, wherein the catheter is configured to fit around the guidewire, and wherein the endograft valve device is configured to fit around the catheter. In another embodiment, the catheter comprises a balloon catheter.

In at least one exemplary embodiment of a method of using an endograft valve device of the present disclosure, the method comprises the steps of introducing a guidewire into a luminal organ of a patient, advancing an endograft valve device along the guidewire to a desired location within the luminal organ, and expanding the endograft valve device within the luminal organ at a first location, wherein operation of the endograft valve device increases a velocity of blood flowing through the blood vessel at the first location. In another embodiment, the method further comprises the step of withdrawing the guidewire from the luminal organ. In yet another embodiment, the luminal organ is a vein, and wherein the endograft valve device is configured as a venous endograft valve device. In an additional embodiment, the step of expanding the endograft valve device comprises expanding the endograft valve device comprising an endograft body configured for expansion within a luminal organ and comprising (i) a first portion having a proximal end defining a proximal end aperture and a distal end defining a distal end aperture, the first portion configured to increase the velocity of fluid flowing therethrough, (ii) a second portion having a second portion proximal end defining a second portion proximal end aperture and a second portion distal end defining a second portion distal end aperture, wherein the distal end of the first portion is adjacent to the second portion proximal end, and (iii) a valve portion positioned at or near the second portion proximal end, the valve portion configured to receive the fluid flowing through the distal end aperture of the first portion.

In at least one exemplary embodiment of a method of determining whether a patient is suitable for a valve procedure of the present disclosure, the method comprises the steps of obtaining data indicative to a patient's venous geometry at a first location, obtaining data indicative of a flow velocity of blood within a vein of the patient at or near the first location, preparing a digital model of the vein of the patient using the data indicative to the patient's venous geometry and/or the data indicative of the flow velocity to obtain patient venous data, and determining whether the patient is suitable for a valve procedure based at least in part on the patient venous data. In another embodiment, the steps of obtaining data are performed using a detection device selected from the group consisting of a duplex ultrasound device, a computed tomography device, and a magnetic resonance imaging device. In yet another embodiment, the steps of obtaining data are performed using an impedance device selected from the group consisting of an impedance wire and an impedance catheter. In an additional embodiment, the steps of obtaining data are performed using an impedance device comprising a device body and at least four electrodes positioned thereon, the at least four electrodes comprising two electrodes configured to excite an electric field and two electrodes configured to obtain a conductance measurement within the electric field.

In at least one exemplary embodiment of a method of determining whether a patient is suitable for a valve procedure of the present disclosure, the step of preparing the digital model of the vein of the patient is performed using the data indicative to the patient's venous geometry and the data indicative of the flow velocity to obtain patient venous data. In an additional embodiment, the step of preparing the digital model of the vein of the patient is performed using the data indicative to the patient's venous geometry to prepare a first digital model and the data indicative of the flow velocity to prepare a second digital model, wherein the patient venous data is indicative of the first digital model and the second digital model. In yet an additional embodiment, the method further comprises the step of incorporating data indicative of at least one valve into the digital model. In another embodiment, the step of determining whether the patient is suitable for a valve procedure based at least in part on the patient venous data and the data indicative of at least one valve.

In at least one exemplary embodiment of a method of determining whether a patient is suitable for a valve procedure of the present disclosure, the step of determining whether the patient is suitable for a valve procedure is based upon at least patient venous data indicative of flow and shear stress, and wherein an ultimate determination is based upon a comparison of the patient venous data indicative of flow and shear stress to at least one threshold. In another embodiment, the step of preparing a digital model of the vein of the patient further uses data indicative of a level of thrombosis within the patient's vessel geometry. In yet another embodiment, the step of preparing a digital model of the vein of the patient further uses data indicative of a blood rheology property within the patient's vessel geometry.

In at least one exemplary embodiment of an external assist device of the present disclosure, the device comprises a cuff configured to fit around a blood vessel and further configured to periodically compress the blood vessel, and a processor operably coupled to the cuff, the processor configured to control a compression rate and a relaxation rate, wherein when the device is positioned around the blood vessel at a first location, operation of the processor causes the cuff to compress the blood vessel and relax compression of the blood vessel, whereby relaxation at the relaxation rate causes blood to move through the blood vessel at the first location. In another embodiment, the compression rate is slower than the relaxation rate. In yet another embodiment, the device further comprises a power source operably coupled to the cuff, the power source configured to provide power to the cuff and/or the processor to facilitate compression and relaxation of the cuff.

In at least one exemplary embodiment of an external assist device of the present disclosure, the device further comprises a connector coupled to the power source and to the cuff, the connector configured to allow power from the power source to be transmitted therethrough to the cuff. In an additional embodiment, the connector comprises a wire. In yet an additional embodiment, the processor is configured so that the compression rate and the relaxation rate can be changed to a different compression rate and a different relaxation rate. In another embodiment, when the device is positioned distal to a blood vessel valve, operation of the device causes blood to flow through the vessel valve toward the device. In yet another embodiment, the blood vessel valve is selected from the group consisting of a native valve and a prosthetic valve.

In at least one exemplary embodiment of an external assist device of the present disclosure, when the device is positioned around the blood vessel at a first location, the blood flows through the blood vessel at the first location a first rate without operation of the device, and the blood flows through the blood vessel at the first location at a second rate during operation of the device, wherein the second rate is faster than the first rate. In an additional embodiment, when the device is positioned around the blood vessel at a first location, the blood flows through the blood vessel at the first location a first rate range without operation of the device, and the blood flows through the blood vessel at the first location at a second rate range during operation of the device, wherein the second rate range has a faster top rate than the first rate range.

In at least one exemplary embodiment of a method of facilitating blood flow through a blood vessel of the present disclosure, the method comprises the steps of positioning an external assist device around a blood vessel, the external assist device comprising a cuff configured to fit around a blood vessel and further configured to periodically compress the blood vessel, and a processor operably coupled to the cuff, the processor configured to control a compression rate and a relaxation rate, wherein when the device is positioned around the blood vessel at a first location, operation of the processor causes the cuff to compress the blood vessel and relax compression of the blood vessel, whereby relaxation at the relaxation rate causes blood to move through the blood vessel at the first location, and operating the external assist device to alternately compress the blood vessel and relax compression of the blood vessel, wherein relaxation of compression causes blood to flow through the blood vessel. In another embodiment, relaxation of compression causes blood to flow through the blood vessel at a faster rate than a native blood flow rate. In yet another embodiment, the step of operating the external assist device comprises operating the external assist device to alternative compress the blood vessel at a first rate and to relax compression of the blood vessel at a second rate, wherein the second rate is faster than the first rate.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 1 shows a portion of a guidewire used to position an exemplary endograft valve device into a luminal organ, according to at least one exemplary embodiment of the present disclosure;

FIG. 2 shows an endograft valve device in a first configuration positioned over a guidewire, according to at least one exemplary embodiment of the present disclosure;

FIG. 3 shows an endograft valve device in a second configuration positioned over a guidewire, according to at least one exemplary embodiment of the present disclosure;

FIG. 4 shows an endograft valve device in a second configuration, according to at least one exemplary embodiment of the present disclosure;

FIG. 5 shows fluid velocities (represented by position and length of arrows) when a valve portion of an endograft valve device is open, according to at least one exemplary embodiment of the present disclosure;

FIG. 6 shows fluid velocities (represented by position and length of arrows) when a valve portion of an endograft valve device is partially closed, according to at least one exemplary embodiment of the present disclosure;

FIG. 7A shows a block diagram of components of a valve system, according to at least one exemplary embodiment of the present disclosure;

FIG. 7B shows an exemplary impedance device, according to at least one exemplary embodiment of the present disclosure;

FIGS. 14A-14C show computer models of a valve portion of a device and a flow field during opening, closing, and closed stages, respectively, according to at least one exemplary embodiment of the present disclosure;

Figure 8:
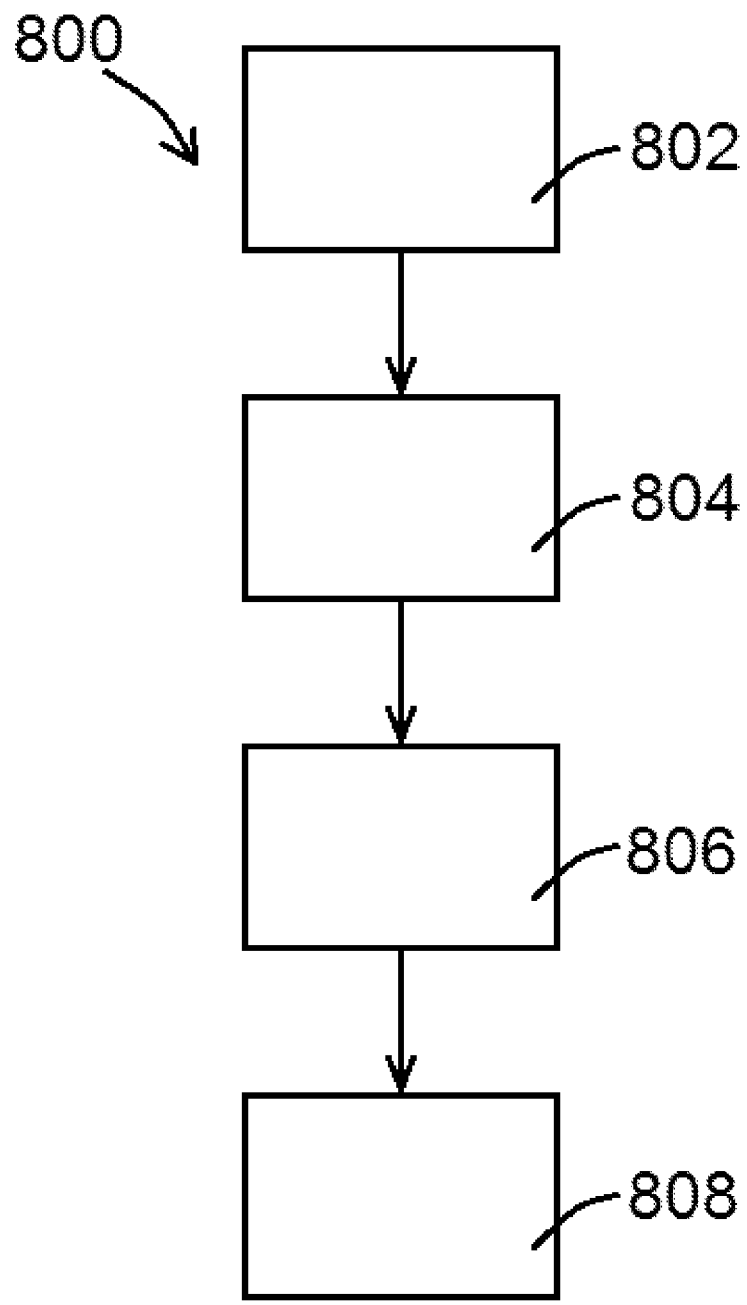
FIG. 8 shows a diagram of method steps, according to at least one exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

With respect to patient treatment for valve and/or venous insufficiency, the disclosure of the present application includes a strategy based on the following three pillars, namely (1) that valve insufficiency must be treated, (2) that no particular therapy can apply to the entire patient population given the various stages of venous insufficiency and the complex etiology thereof, and (3) that no valve can function long-term in the absence of flow (and more specifically shear stress). The present disclosure addresses each pillar.

The first pillar (namely that valve insufficiency must be treated) is addressed by way of one or more exemplary endograft valve devices.

Shear Enhancing Valve

An exemplary endograft valve device 100 of the present disclosure is described as follows. As shown in FIG. 3, for example, an exemplary valve device 100 of the present disclosure comprises an endograft body 102 having a first portion 104, a second portion 106, and a valve portion 108. Endograft body 102, in various embodiments, is configured to fit within a luminal organ and further configured for expansion within the luminal organ. The first portion 104 of the endograft body 102, as shown in FIG. 3 in an expanded configuration, has a proximal end 110 defining a proximal end aperture 112 and a distal end 114 defining a distal end aperture 116, the first portion 104 tapering toward distal end 114 so that distal end aperture 116 has a relatively smaller cross-sectional area than proximal end aperture 112. Second portion 106 of the endograft body 102, as shown in FIG. 3 in an expanded configuration, also has a proximal end 118 defining a proximal end aperture 120 and a distal end 122 defining a distal end aperture 124, the second portion 106 tapering toward distal end 122 so that distal end aperture 124 has a relatively smaller cross-sectional area than proximal end aperture 120. As shown in FIG. 3, and in various embodiments of the present disclosure, distal end 114 of first portion 104 is positioned adjacent to (and/or coupled to) proximal end 118 of second portion 106. Valve portion 108, as referenced above and shown in FIGS. 3 and 4 for example, is positioned at or near proximal end 118 of second portion 106 (or coupled to first portion 104 or second portion 106), wherein valve portion 108 is configured to receive fluid flowing through distal end aperture 116 of first portion 104. Valve portion 108 connection to endograft body 102, for example, can be by way of various anchoring mechanisms useful within the graft/stent arts, such as by using magnets, surfaces having certain friction characteristics, hooks, and/or other securing means. As referenced herein, valve portion 108 is "stentless" in that it is not coupled or connected to a stent. Instead, a valve portion 108 of an exemplary endograft valve device 100 of the present disclosure are supported by endograft body 102 and/or another portion of endograft valve device 100, which provides an advantage over the stent arts as stent struts tend to elicit a negative biological response.

An exemplary endograft valve device 100 of the present disclosure may be positioned within a luminal organ of a patient as follows. In at least one embodiment, and as shown in FIG. 1, a guidewire 200 having an optional compliant end 202 may be inserted into a lumen 250 of a luminal organ 252 of a patient. In at least one embodiment, luminal organ 252 comprises a patient's vein, and an exemplary endograft valve device 100 of the present disclosure is configured to fit within the patient's vein and configured to operate in accordance with the present disclosure.

Upon insertion and placement of a portion of a guidewire 200 within a luminal organ 252, an exemplary endograft valve device 100 of the present disclosure may be advanced over guidewire 200 to a desired location within luminal organ 252 as shown in FIG. 2. As shown in FIG. 2, endograft valve device 100 is in a first, or collapsed, configuration, and as shown in FIG. 3, endograft valve device 100 is in a second, or expanded, configuration. Endograft valve device 100 may be positioned around and/or coupled to an optional catheter 260, as shown in FIG. 2, to facilitate positioning of endograft valve device 100 within luminal organ 252. Expansion of endograft valve device 100 may be due to movement of guidewire 200, movement of optional catheter 260, inflation of a balloon 702 (as shown in FIG. 7, for example) positioned upon catheter 260, or other mechanisms/procedures known to facilitate expansion of an endograft and/or stent.

A side view of an exemplary endograft valve device 100 is shown in FIG. 2, while a cross-sectional side view of an exemplary endograft valve device 100 is shown in FIG. 3. Expansion of endograft valve device 100 (from FIG. 2 to FIG. 3) causes at least a portion of endograft valve device 100 to physically contact luminal organ 252 as shown in FIG. 3. As shown in FIG. 3, an outer portion 300 of endograft valve device 100 contacts luminal organ 252, while an inner portion 302 of endograft valve device 100 is configured so that fluid may flow therethrough and through valve portion 108. Outer portion 300 may generally define an outer portion wall 310, and inner portion 302 may generally define an inner portion wall 312, as shown in FIG. 3. In at least one embodiment, outer portion wall 310 and/or inner portion wall 312 may be relative walls, as endograft body 102 may itself comprise a mesh that does not create a formal wall. In such an embodiment, for example, outer portion 300 may define an outer portion relative surface 320, and inner portion 302 may define an inner portion relative surface 322, as shown in FIG. 4. As shown in each of FIGS. 3 and 4, the interior portion of an exemplary endograft valve device 100 is generally referred to as a lumen 350, whereby lumen 350 tapers toward distal end 114 of first portion 104 and again tapers toward distal end 122 of second portion 106.

FIG. 4 shows an exemplary endograft valve device 100 positioned within a lumen 250 of a luminal organ 252 with guidewire 200 and optional catheter 260 withdrawn. FIG. 4 shows "CSA1" and "CSA2," which are indicative of a first cross-sectional area and a second cross-sectional area, respectively. As shown in FIG. 4, CSA1 is relatively larger than CSA2, with CSA1 being indicative of a proximal end aperture 112 of first portion 104, and with CSA2 being indicative of a distal end aperture 116 of first portion 104. As shown therein, first portion 104 tapers inward toward valve portion 108.

Valve portion 108, as generally referenced above, is configured in at least one embodiment as a venous valve system. In at exemplary embodiment, valve portion 108 is configured as an effective bicuspid valve system for a vein, noting that the arterial system has substantially higher shear stresses than the venous system. In view of the same, exemplary valve portions 108 of the present disclosure are configured to increase shear stress at the leaflets 500 of valve portion 108 as shown in FIG. 5 so that they effectively operate as venous valves.

As shown in FIGS. 3-6, exemplary endograft valve devices 100 are provided for potential use within a patient's body instead of a traditional stent that may carry a valve. As generally referenced above and shown in FIGS. 3-6, endograft valve devices 100 are configured to taper endoluminally, either linerally as shown in the figures or in some other fashion, so that blood flowing therethrough will increase in velocity and hence increase the shear stress at valve portion 108.

Conservation of mass requires that volumetric flow rate (Q) to remain constant throughout the graft (i.e., Q=constant=V*CSA, where V and CSA represent the velocity of blood and luminal cross-sectional area of the endograft). Since the CSA is made, by novel design of the various endograft valve devices 100 of the present disclosure, to decrease towards valve portion 108 (i.e., CSA2<CSA1 as shown in FIG. 4), the velocity will be much larger at valve portion 108. The wall shear stress (WSS, referring to the stresses of inner portion 302 of endograft valve device 100) is related to the CSA as WSS~1/CSA3/2 (Poiseuille's law) and hence any decrease in CSA will amplify the WSS. For example, a 10% decrease in diameter (CSA~D2) is expected to increase the WSS by 33%.

The increase in WSS and the corresponding reduction in thrombogenecity at the valve is weighted against the potential increase in the pressure drop (ΔP, as shown in FIG. 5) to overcome the resistance to flow. A 50% decrease in CSA, for example is non-flow limiting (i.e., only a minimal pressure drop). Hence, even at this level of CSA design, the WSS can be nearly tripled (~2.8×). A reverse tapering on the distal portion of the valve, in at least one embodiment and as shown in FIG. 6, is considered to ensure flow recirculation and hence the establishment of a negative pressure drop to close valve portion 108.

Endograft valve devices 100 of the present disclosure may be configured as follows. In various embodiments, endograft body 102 should have a length at least greater than the diameter of the vein (or other vessel/luminal organ to receive endograft body 102) so to prevent rotation of endograft valve device 100 within the lumen 250 of luminal organ 250. In at least one embodiment, the length of endograft body 102 is at least three times the diameter of the vein. Valve portion 108, in various embodiments, would be at or near the center of endograft body 102.

Regarding placement of exemplary endograft valve devices 100 of the present disclosure within lumens 250 of luminal organs 252 (such as veins), a coaptation length (length of endograft valve device 100 contact with luminal organ 252) of no less than 4 mm, and as little as between 4-5 mm, is generally sufficient so to ensure good operation (closure, for example), of valve portion 108. A coaptation length of 4-5 mm, for example, is approximately half of a diameter of the luminal organ 252 in at least one example, noting that a lesser coaptation length relative to the diameter of luminal organ 252, such as approximately ⅓ of the diameter, also suffices in certain embodiments. In various embodiments, the radius of the dome of valve portion 108 is at least approximately half of the radius of luminal organ 252 (or at least approximately one fourth of the diameter of luminal organ 252).

The present disclosure considers various hemodynamic variables to ensure a correct design that prevents stasis. The third point of the triad, namely changes in the vessel wall as referenced herein, can be considered as various endograft valve devices 100 can be coated similarly to a luminal organ (such as a biological vein, for example) at least acutely until the endograft valve device 100 endothelializes. Such considerations may require that the inner portion 302 (such as inner portion wall 312 or inner portion relative surface 322, for example) of the endograft valve device 100 be at least partially covered or coated one or more anti-clotting agents including, but not limited to, heparin, thrombomodulin, endothelial cell protein C, and/or another anti-clotting agent, and/or one or more anti-inflammatory agents including, but not limited to, protease inhibitor(s), α1-antitrypsin, α1-macroglobulin, α1-antichymotrypsin, and/or another anti-inflammatory drug. FIG. 5 shows agent 510 positioned upon endograft valve device 100. In addition to providing an anticoagulant endoluminal surface (such as inner portion wall 312 or inner portion relative surface 322, for example), the same can also be provided to the endograft outer portion 300 (such as outer portion wall 310 or outer portion relative surface 320, for example) to dissolve any existing clots in the luminal organ upon deployment of the endograft valve device 100.

Various embodiments of endograft valve devices 100 of the present disclosure may be made of one or more standard biologically-compatible materials, such as polytetrafluoroethylene (PTFE), Gore-Tex®, etc., containing, for example, a nickel titanium alloy such as nitinol and/or another memory metal in the endograft body 102 so that the desired memory shape of the endograft valve device 100, in an open or a closed configuration, is accomplished while maintaining the desired hemodynamic effects noted above.

At least one exemplary embodiment of a valve system 700 of the present disclosure is shown in the block diagram of FIG. 7. As shown in FIG. 7, an exemplary valve system 700 comprises a number of components of an exemplary endograft valve device 100 of the present disclosure, such as endograft body 102, valve portion 108, etc. In addition, an exemplary valve system 700 may comprise one or more components useful to deliver and/or position an exemplary valve device 100 of the present disclosure, including a guidewire 200, a catheter 260, and an optional balloon 702 coupled to or positioned adjacent to catheter 260.

FIG. 8 shows a diagram of steps of an exemplary method of using an endograft valve device 100 and/or valve system 700 of the present disclosure. As shown in FIG. 8, an exemplary method 800 comprises the steps of introducing a guidewire into a luminal organ (such as a vein) of a patient (an exemplary guidewire insertion step 802) and advancing an endograft valve device 100 along guidewire 200 to a desired location within a patient (an exemplary advancement step 804). Endograft valve device 100 is then expanded as referenced herein (an exemplary expansion step 806), and the guidewire 200 and/or any other device used to deliver endograft valve device 100 (such as a catheter 260, for example), is withdrawn from the area of the endograft valve device 100 (an exemplary removal step 808).

The second pillar, namely that no particular therapy can apply to the entire patient population given the various stages of venous insufficiency and the complex etiology thereof, is addressed as follows.

Patient-Specific Virtual Venous Valve Simulation

An analogy can be drawn with mitral valve and heart failure (HF) whose etiology may be of ischemic, electrical, or valvular origin. A number of therapies for HF exist, such as revascularization (including coronary artery bypass graft (CABG) surgery and percutaneous coronary intervention (PCI)), valve replacement, cardiac resynchronization therapy (CRT), use of a left ventricular assist device (LVAD), and the like. Each of these therapies has guidelines for patient selection (inclusion/exclusion criterion). A similar paradigm for patient selection must be established for venous insufficiency in order for a therapy to be effective.

Since no particular therapy can apply to the entire patient population given the various stages of venous insufficiency and the complex etiology thereof, the development and use of methods and algorithms for proper selection of patients that optimize efficacy becomes increasingly important. In particular, appropriate mechanical forces are necessary to ensure that an implantable device having a valve, such as valve portion 108 of an exemplary endograft valve device 100, that can function in the long-term with respect to maximum shear stress and minimum wall stress, for example. The disclosure of the present application includes the use of a number of variables such as, for example, values of wall stress, wall shear stress (WSS), gradient of WSS (WSSG), oscillatory shear index (OSI), and other hemodynamic parameters to decide patient selection for potential venous valve therapy. As certain biochemical cell responses (such as responses of endothelium, mesothelium, epithelium, smooth muscles, thrombosis, etc.) can be identified, the relation between the aforementioned variables/parameters can be used to provide optimized hemodynamic conditions to elicit optimal function of the cells.

The disclosure of the present application includes a patient-specific, physics-based approach to determine whether or not the patient is suitable for a potential vein valve procedure. Such an approach, in at least one embodiment, may be useful to develop a validated, patient-specific, physics-based computational model to predict the clinical function of a prosthetic valve replacement device. Existing clinical imaging modality, such as duplex ultrasonography (US) may be used in connection therewith to provide both the venous geometry and flow velocity of a patient.

The patient-specific, physics-based approach referenced above can be used not only to determine whether or not a patient is suitable for a potential vein valve procedure, but also to determine whether or not a patient is suitable for treatment using one or more given valves or implantable valve devices (such as an exemplary endograft valve device 100 of the present disclosure). In addition to duplex US referenced above, and if three-dimensional geometry is required, computed tomography (CT) and/or magnetic resonance imaging (MRI) can provide such data.

Figure 13:
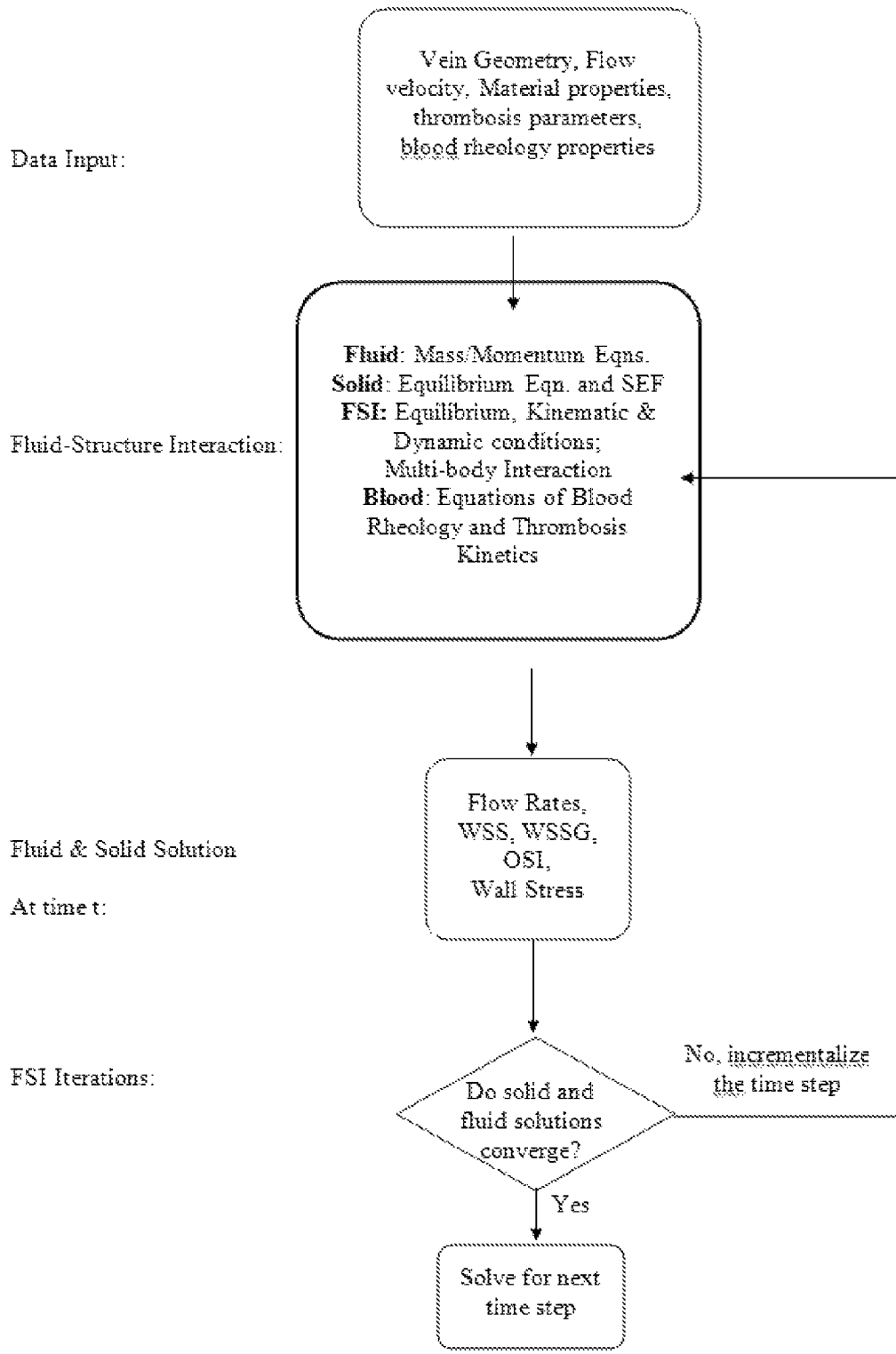
FIG. 13 shows a flow chart of steps in connection with an exemplary fluid-structure interaction algorithm, according to at least one exemplary embodiment of the present disclosure.

An exemplary patient selection method of the present disclosure uses one or more computer models of various venous valves, whereby said valves can be virtually implanted into a model of the specific patient's geometry and flow boundary conditions, such as shown in the flow chart shown in FIG. 13. Various laws of physics, such as the conservation of mass and momentum, and blood rheology and thrombosis kinetics can be used in conjunction with the patient-specific boundary condition (flow velocity) to simulate the entire velocity and shear field on the valve leaflets as well as the mechanical stresses and strains in the leaflets and/or other functional surfaces of the devices. As referenced within FIG. 13, "FSI" indicates a fluid-structure interaction, "WSS" indicates wall shear stress, "WSSG" indicates wall shear stress gradient, "OSI" indicates oscillatory shear index, and "SEF" indicates a strain energy function.

As shown in FIG. 13, various inputs (as provided in further detail herein in connection with FIG. 17) can be utilized, along with a series of fluid, solid, FSI, and blood relationships in connection with the interactions as referenced above, at any given time, leading to a FSI iteration as to whether or not the solid and fluid solutions converge at that particular step. Should there be no convergence, the time step can be incrementalized, and the inputs, relationships, and/or interactions can be repeated/reacquired to repeat the FSI iteration if desired. Should there be a convergence, the next step in a given model/process can be performed.

Various sample prototype devices may also be tested in said simulations, providing data indicative of the temporal and spatial distributions of the stresses. These simulations would then provide the physical predictions of the expected levels of the mechanical environment of the prototype valves and their propensities for success or failure based, in part, on the various intramural stresses and strains in the valve device materials.

By way of example, patients that have low shear stresses (i.e., stasis) on the valve leaflets can be excluded since these patients are likely to have a poor outcome. The relation between the cutoff for the various mechanical forces, deformations, and biological responses can be determined through in vivo experiments that include realistic models of venous hypertension and insufficiency (e.g., venous hypertension using an arteriovenous (AV) fistula and occlusion models to perturb flow and shear stress and evaluate the biological response of the valve implant). Such relationships can then be leveraged to select only those patients with physical or biochemical (including blood chemistry, thrombogenecity, clotting factors, etc.) conditions. Hence, various guidelines and criterion for acceptable mechanical regimes in animal studies and from the published literature can be established and used to guide the initial patient experience.

Exemplary computational platforms for both fluid and solid mechanics of a valve can be obtained using duplex US, an impedance device (as referenced below), or another mechanism useful to obtain geometric and flow data of a valve within a vessel. Such a computer simulation of a flow field and wall stress can be generated for an idealized valve with idealized geometries and flows, and said platforms can then be repeated for specific patients, so that flows and stresses representative of a specific patient can be provided.

As can be identified by such a platform, idealized valves prominently show regions of stagnant flow in the base region of the valve under the provided flow conditions, as well as showing flow alterations at the hinge region of leaflets. Flow rates and direction can then be indicated using a series of arrows to show direction of flow (via arrow point) within a vessel and rate of flow (as given by the overall length of the arrows). A longer arrow denotes a faster flow rate. Wall stresses can be shown using, for example, various colors or pixel concentrations to show areas with higher stresses (generally at or near the valve leaflets) and areas of lower stresses (generally away from the valve leaflets).

Examples of both fluid (flow velocity) and solid mechanics (wall stress) of exemplary valve computational results are shown in FIGS. 14A-14C and FIGS. 15A-15B, respectively for exemplary idealized geometries, flows, etc. As shown within such simulations of an exemplary idealized valve (referred to herein as a valve portion 108 of an endograft valve device 100, for example), the regions of stagnant flow in the base region of the valve are more which are typically prone to platelet/thrombus accumulation. There are also flow alterations at the hinge region of leaflets as depicted therein, and high wall stresses, for example, would also tend to map with lipid/calcification deposition pattern.

The flow fields during opening, closing and closed stages are shown in FIGS. 14A-14C, respectively. Flow accelerates during valve opening when a jet forms at center of the flow. Behind the leaflets (such as leaflets 500 of valve portion 108 of an exemplary endograft valve device 100 of the present disclosure), vortices form which promote shear stress on the leaflet surface, as shown in FIG. 14A. Flow decelerates during valve closure and well-defined vortices are observed during this stage as well, suggesting that the leaflet dome is inducive to vortex formation, as shown in FIG. 14B. Flow ceases when the valve is fully closed, and only a minimal amount of flow is observed upstream, as shown in FIG. 14C.

Figure 15A:
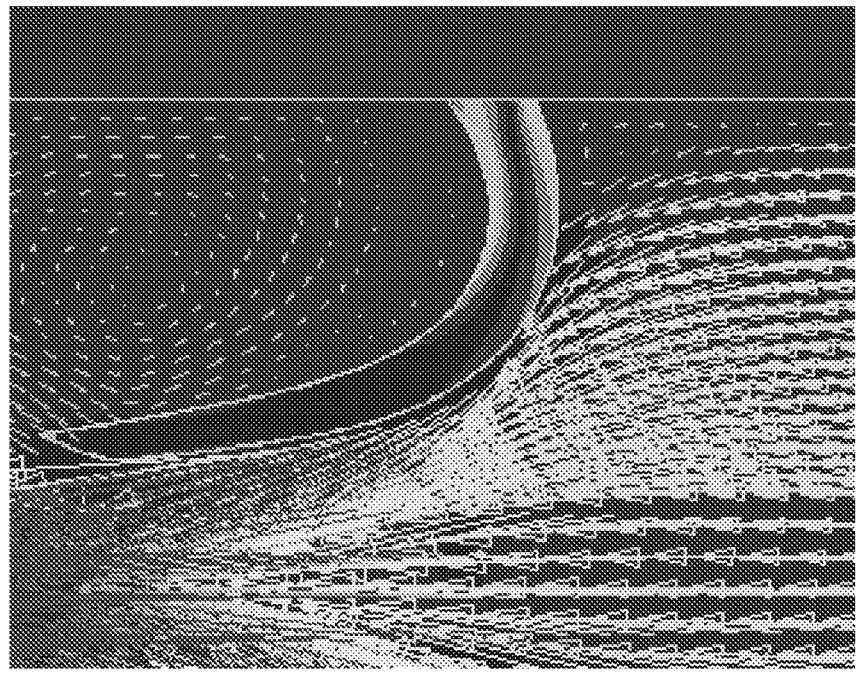
FIGS. 15A and 15B show computer models of a valve portion of a device with intramural stress concentrations on the leaflets in addition to the flow field during opening and closed stages, respectively, according to at least one exemplary embodiment of the present disclosure.
Figure 15B:
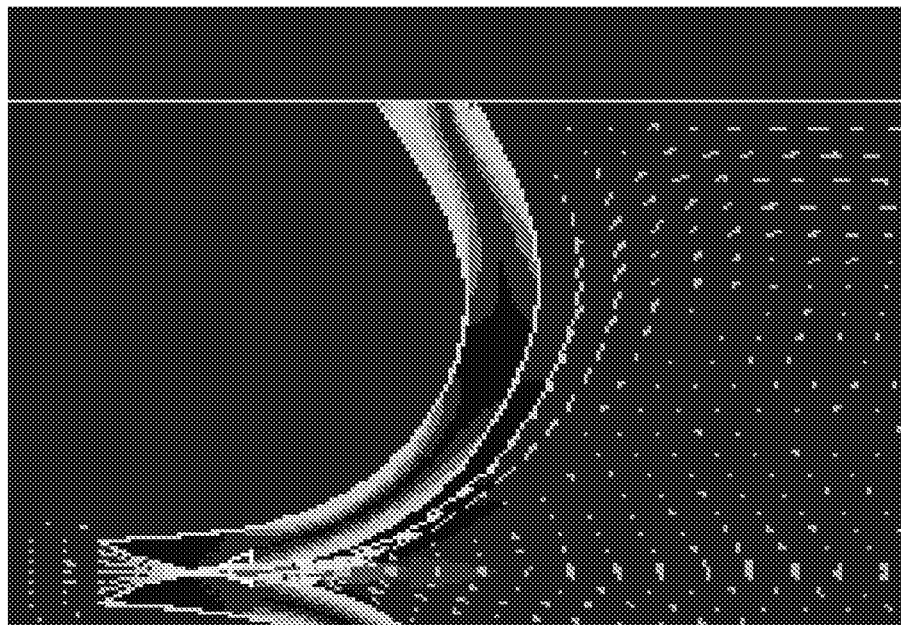

The intramural wall stress concentrations on the leaflets are shown in FIGS. 15A and 15B. The stresses concentrate at the base region (the lighter regions shown therein) during various stages of leaflet motion. The base regions also experience the least amount of flow and shear. Thus, this region has the compounded effect of high intramural stress and low endothelial shear. As the result, the mechanical cost function (ratio of wall stress to fluid shear stress) was particularly high at the base.

Figure 16:
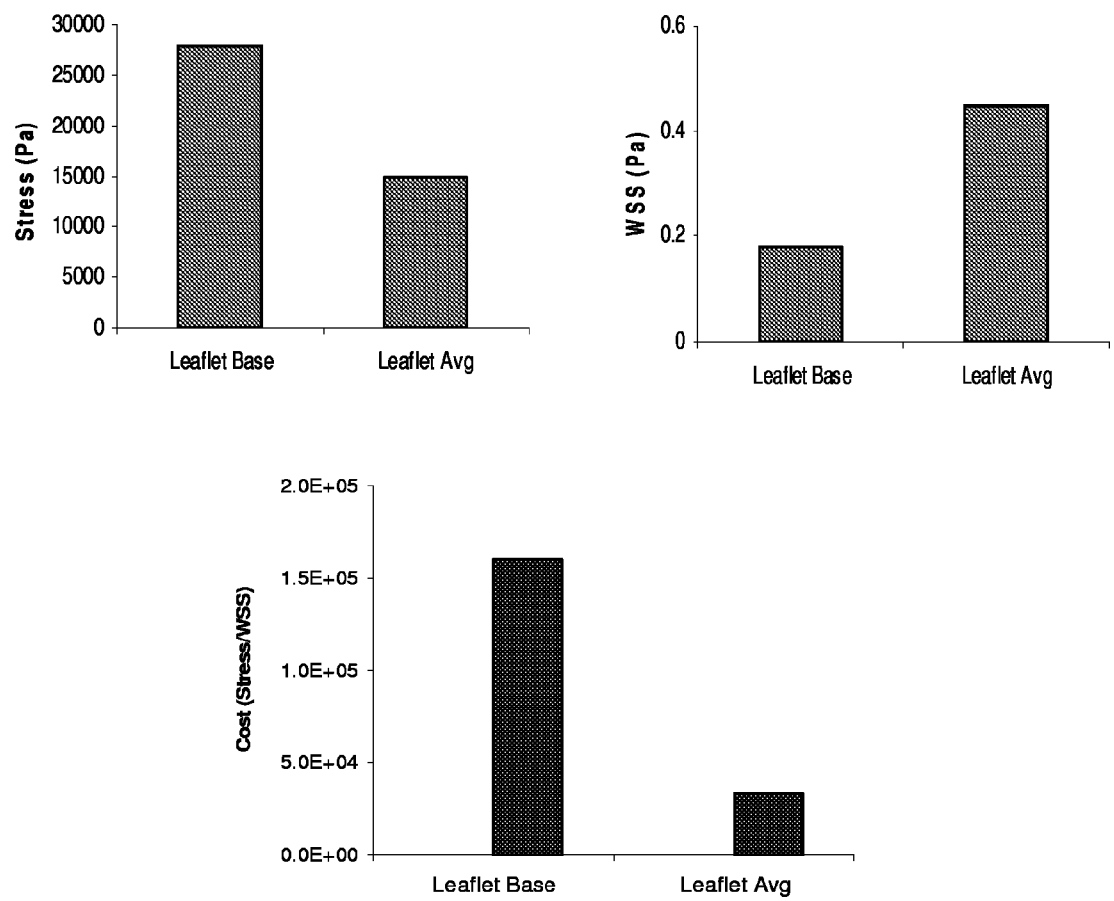
FIG. 16 shows the stress, WSS, and mechanical cost at the valve leaflet versus the leaflet averages, according to at least one exemplary embodiment of the present disclosure.

The cost at leaflet base was about five times higher than the leaflet average, as shown in FIG. 16. This predicts the high rate of pathological events at the base. The vast majority of the implanted venous valves present disease initiation and progression at the base. Hence, the algorithm predictions (as referenced in further detail below) are consistent with clinical experience.

In view of the foregoing, and for example, if the vessel geometry and flow are identified and plugged into the model, the model can identify, even without incorporating a model endograft valve device 100 of the present disclosure therein, that a geometry with diameter less than or approximately 8 mm, for example, or a cross-sectional area less than or approximately 0.5 $cm^2$, for example, would disqualify a patient from potential treatment. Similarly, blood flow velocity less than or approximately 30 ml/min may be too low, as a goal is to have the velocity greater than or approximately 50 ml/min or ideally or approximately 150 ml/min, for example.

Figure 17:
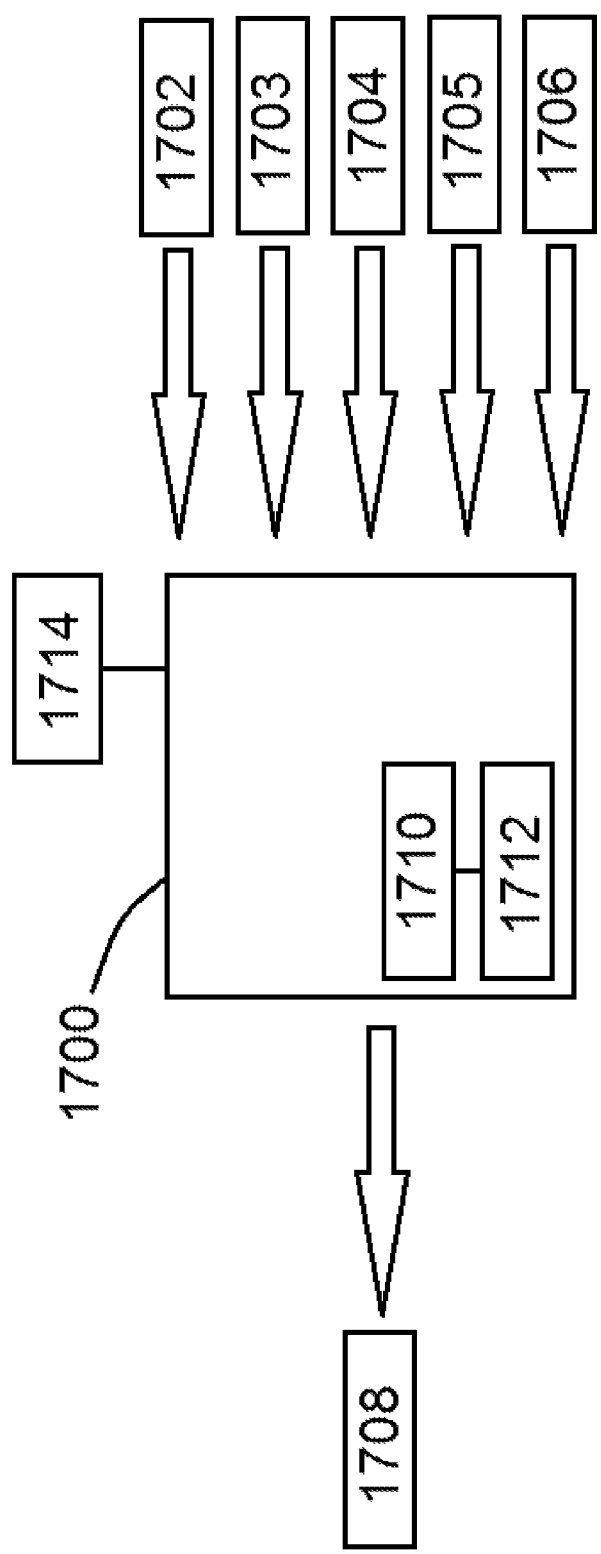
FIG. 17 shows a component block diagram of a digital model, according to at least one exemplary embodiment of the present disclosure.

To depict the foregoing, an exemplary digital model 1700 of the present disclosure is shown in the block diagram of FIG. 17. As shown therein, digital model 1700 can utilize a number of pieces of information as inputs, such as vessel geometry (as vessel geometry input 1702), blood flow velocity (as flow velocity input 1704), and information relating to an actual or proposed (digital) valve portion 108 and/or endograft valve device 100 (as valve input 1706). Additional inputs, such as those relating to a level of thrombosis within the vessel geometry (as thrombosis input 1703), and/or relating to a blood rheology property (as rheology input 1705), as shown in FIG. 13, can be used within exemplary digital models 1700 of the present disclosure. Said information relating to an actual or proposed digital valve can include valve inputs 1706 relating to endograft valve device 100 dimensions (length, width, diameters, cross-sectional areas, etc. of various portions of the same) and, in particular, for example, to characteristics of valve portion 108, such as values of wall stress, wall shear stress (WSS), gradient of WSS (WSSG), oscillatory shear index (OSI), leaflet characteristics, and the like.

Digital model 1700, having the various inputs 1702, 1704, and 1706 therein, can generate a number of model outputs 1708 as shown in FIG. 17. Model outputs 1708, in various embodiments, can include outputs 1708 relating to whether or not a patient is suitable for a valve procedure, and if so and depending on the valve input(s) 1706 in digital model 1700, model outputs 1708 can indicate whether or not a particular valve model (within valve input 1706) would operate as desired in order to treat the patient.

Exemplary outputs 1708 can be generated by way of operation of a processor 1710 (as referenced below) of digital model 1700, whereby processor 1710 processes one or more inputs to generate said model output(s) 1708. The processing of said inputs may include processing in view of one or more relationships referenced within the present disclosure, such as those selected from the group consisting of a fluid relationship (relating to mass and/or momentum), a solid relationship (relating to an equilibrium equation and a strain energy function), a fluid-structure interaction relationship (including equilibrium, kinematic, and dynamic conditions, as well as multi-body interaction), and a blood relationship including equations of blood rheology and/or thrombosis kinetics), to generate one or more model outputs 1708. Model output 1708 generation of the present disclosure is not limited to the aforementioned relationships.

Example 1

For a particular location within a patient's venous system, the patient has a luminal organ 252 diameter of 1.0 cm and blood flow velocity of 20 ml/min. By incorporating the diameter (as vessel geometry input 1702) and the flow velocity (as flow velocity input 1704) into digital model 1700, digital model 1700 can process said inputs 1702, 1704 and generate a model output 1708 indicating that the patient is not suitable for a valve procedure based upon, for example the flow velocity being below a threshold require flow velocity (20 ml/min, as compared to an exemplary threshold velocity of 30 ml/min).

Example 2

For a particular location within a patient's venous system, the patient has a luminal organ 252 diameter of 1.0 cm and blood flow velocity of 35 ml/min. By incorporating the diameter (as vessel geometry input 1702) and the flow velocity (as flow velocity input 1704) into digital model 1700, digital model 1700 can process said inputs 1702, 1704 and generate a model output 1708 indicating that the patient is suitable for a valve procedure based upon, for example the diameter and flow velocity being at or above threshold values of, for example, 0.8 cm and 30 ml/min, respectively. A first model valve (valve portion 108 and/or endograft valve device 100) can be digitally incorporated into digital model 1700 as one or more valve inputs 1706, and operation of digital model 1700 in view of valve input(s) 1706 can generate model output(s) 1708 indicating whether or not the first model valve would be sufficient to treat the patient. By way of example, operation of digital model 1700 may identify certain WSS, WSSG, OSI, leaflet 500 characteristics, and/or other data indicative of valve input(s) 1706 within digital model 1700 relative to vessel geometry input(s) 1702 and flow velocity input(s) 1704 in determining the ultimate model output(s) 1708. Furthermore, operation of digital model 1700 may identify changes in flow velocity (up or down), and said changes can be used to determine the model output(s) 1708. If the first model valve, for example, results in one more desired WSS, WSSG, OSI, leaflet 500 characteristics, and/or flow velocity characteristics, model output(s) 1708 can indicate whether or not to proceed with treating the patient using a valve portion 108 or an endograft valve device 100 having characteristics of the first model valve. For example, the WSS, determined based upon valve input(s) 1706, can be identified as being within a desired range (such as, for example, greater than or about 5 dynes/cm$^2$ and less than or about 10 dynes/cm$^2$), which could provide a model output 1708 identifying the likelihood of success of operation of a valve portion 108 or endograft valve device 100 having such WSS values in connection with inputs 1702 and 1704. Furthermore, model outputs(s) 1708 can include specific numerical and/or visual results with respect to WSS, WSSG, OSI, leaflet 500 characteristics, and/or flow velocity characteristics, which can lead to changes in the model valves so that, for example, a second model valve can be incorporated into digital model 1700 as a second valve input 1706, with the second model valve being modified relative to the first model valve based on the model output(s) 1708 relating to the first model valve. This process can be repeated until an optimal valve portion 108 and/or endograft valve device 100 model is identified, and an actual valve portion 108 and/or endograft valve device 100 can be used, based upon the identified model, to treat the patient with a high likelihood of success based upon the model output(s).

In summary, an exemplary digital model 1700 of the present disclosure relates to patent vessel geometry and fluid flows therein when various digital valve/device models are applied thereto. In patients with developed fibrosis within a lumen 250, for example, such fibrosis may hinder proper valve portion 108 operation. Various imaging systems, such as CT or MRE, can be useful to determine three dimensional geometries to identify such fibrotic environments as being environments less optimal for valve portion 108 or endograft valve device 100 implantation.

In addition, and as shown in FIG. 17, digital model 1700 may comprise a number of elements found in our useful with a laboratory computer. For example, and in order to process various inputs 1702, 1704, and 1706, digital model 1700 may include/comprise a processor 1710 operably coupled to a storage medium 1712, whereby data inputted into digital model 1700 can be processed using processor 1710, and the processed data (such as model output(s) 1708, other processed data) and/or the various inputs 1702, 1704, 1706 can be stored in storage medium 1712 and accessed later on if desired. Model output(s) 1708, in various formats, can be displayed on a display 1714, for example, operably coupled to, or part of, digital model 1700

As noted above, and to minimize ad hoc assumptions in the simulations, accurate data would be established based upon the anatomy (geometry) and material properties of both the potentially-used prosthetic valve and the vein itself. Furthermore, and in addition to duplex US, additional technologies (such as impedance wires and catheters, for example) can be leveraged to determine both the size of the vein to match the prosthesis (to prevent migration) as well as compliance of the vessel (for accurate simulation of vein wall motion and coupling to blood flow). Such a tailored approach, for example, can be used to define the range of in vivo performance of the valve in a patient-specific mechanical environment. Additional factors beyond mechanics, such as blood chemistry, can also be considered in light of mathematical models of thrombosis.

As such, the various virtual simulations used to test various device/valve designs would allow researchers to design and redesign such devices until the devices/valves have the desired functionality. Specific devices/valves, including those specific to venous diseases, can be optimized so that their use in vivo would be effective for any number of luminal organ needs.

The governing equations for the fluid domain are the Navier-stokes & Continuity equations.

$$\frac{\partial \vec{V}}{\partial t} + \vec{V} \cdot \vec{\nabla} \vec{V} + \frac{\vec{\nabla} p}{\rho} - 2\frac{\eta}{\rho} \vec{\nabla} \cdot D = \vec{0} \qquad \text{Equation [1]}$$

$$\vec{\nabla} \cdot \vec{V} = 0 \qquad \text{Equation [2]}$$

Wherein V is velocity, P is pressure, $\rho$ is density, $\eta$ is viscosity, D is the rate of deformation tensor, and $\vec{\nabla}$ is the gradient operator.

The governing equations for the solid domain were the Momentum and Equilibrium equations; i.e., Newton's laws of Mechanics:

$$\rho a_i - \sigma_{ij,j} - \rho f_i = 0 \text{ in } {}^s\Omega(t) \qquad \text{Equation [3]}$$

$$\sigma_{ij} n_j - t_i = 0 \text{ on } {}^s\Gamma(t) \qquad \text{Equation [4]}$$

where $a_i$ is acceleration, $f_i$ is force per unit mass, ${}^s\Omega(t)$ is the vessel domain at time t, $n_j$ is normal vector, $t_i$ is surface traction vector, and $\sigma_{ij}$ is stress. A number of models exist to describe the blood rheology that relates WSS to shear rate, vessel diameter, blood hematocrit, and thrombosis kinetics. Those formulations are used in conjunctions with the equations of state prescribed above.

For an exemplary model, the vessel lumen and valve were 10 mm in diameter, representative of a typical femoral vein and valve. The fluid was modeled as incompressible with pulsatile flow of 20 beats per minute. The density and viscosity were 1050 kg/m$^3$ and 0.004 kg/m·s respectively. For the wall interface, no slip between fluid and the wall and no permeability of the vessel wall were assumed.

To model the interaction of leaflets during closure, contact or multi-body interaction was setup between the approaching leaflets. The Augmented Lagrange algorithm was applied, and penetrations between the leaflet surfaces were not allowed by the contact algorithm. Once penetration was detected, the overlapping elements were returned to their positions at the previous time step.

Fluid-structure interfaces were defined at the surfaces of the leaflets and boundaries of the fluid. The Arbitary Lagrange-Eulerian (ALE) method was used, which allows the fluid mesh to deform around the moving leaflets, which is necessary for an application with the large deformation. Instead of using either a single Lagrangian approach or a single Eulerian approach, the ALE describes the motion of fluid in a moving reference frame with the constraint that the velocity on the fluid-solid boundary must equal to that of the boundary.

The Navier-Stoke equations for the fluid and the momentum and equilibrium equations for the solid are coupled on the fluid-solid interface via the kinematic and dynamic conditions, as shown in FIG. 16. The boundary condition can be either the flow velocity or the pressure gradient, for example. The solid and fluid models were coupled by the fluid nodal positions on the fluid-structure interaction (FSI) interfaces which are determined by the kinematic conditions. The displacements of the other fluid nodes were determined so as to preserve the initial mesh quality. The ALE modified governing equations for fluid flow were then solved. For the dynamic case, the fluid stresses were integrated along the fluid-solid interface and applied on the corresponding solid nodes. The fully coupled 2-way FSI model was solved, and the solution process continued until solutions for solid and fluid nodes converge on the FSI interface and steady solution was achieved (as shown in FIG. 16).

For the valve optimization, since WSS has an inverse relation with intimal hyperplasia (IH) and thrombosis, Stress/WSS was used as the cost function. To combine the solid and fluid parameters, addition or subtraction is not appropriate, as the solid and fluid stresses are orders of magnitude different (i.e., KPa vs. Pa).

Accordingly, the present disclosure includes disclosure of a method of determining whether a patient is suitable for a valve procedure. In at least one embodiment of a method 900, as indicated by the method steps shown in FIG. 9A, method 900 comprises the steps of obtaining data indicative to a patient's venous geometry at a first location (an exemplary first data obtaining step 902) and obtaining data indicative of a flow velocity of blood within a vein of the patient at or near the first location (an exemplary second data obtaining step 904), wherein steps 902 and 904 can be performed in either order. Method 900, in various embodiments, further comprises the steps of preparing a digital model 1700 of the vein of the patient using the data indicative to the patient's venous geometry and/or the data indicative of the flow velocity to obtain patient venous data (an exemplary digital model preparation step 906), and determining whether the patient is suitable for a valve procedure based at least in part of the patient venous data (an exemplary determination step 908).

In at least one embodiment, steps 902 and/or 904 is/are performed using duplex ultrasonography and/or another detection device of the present disclosure. As shown in the block diagram in FIG. 9B, an exemplary subsystem 950 of the present disclosure comprises an exemplary endograft valve device 100 of the present disclosure and a device or system for obtaining patient input data, identified generally as a detection device 952. Detection devices 952 of the present disclosure include, but are not limited to, a duplex US device, a computed tomography (CT) device, magnetic resonance imaging (MRI) device, and/or an impedance device 750 as referenced in further detail below.

In various embodiments, steps 902 and/or 904 is/are performed using an impedance device, such as an impedance wire and an impedance catheter. An exemplary impedance device 750, as shown in FIG. 7B, may comprise a device body 752 and at least four electrodes 754, 756, 758, 760 positioned thereon, wherein the at least four electrodes 754, 756, 758, 760 comprise two excitation electrodes 754, 756 configured to excite an electric field and two detection electrodes 758, 760 configured to obtain a conductance measurement within the electric field.

In various embodiments of methods 900 of the present disclosure, digital model preparation step 906 is performed using the data indicative to the patient's venous geometry and the data indicative of the flow velocity to obtain patient venous data. In other embodiments, digital model preparation step 906 is performed using the data indicative to the patient's venous geometry to prepare a first digital model 1700 and the data indicative of the flow velocity to prepare a second digital model 1700, wherein the patient venous data is indicative of the first digital model 1700 and the second digital model 1700.

Figures 9A, 9B:
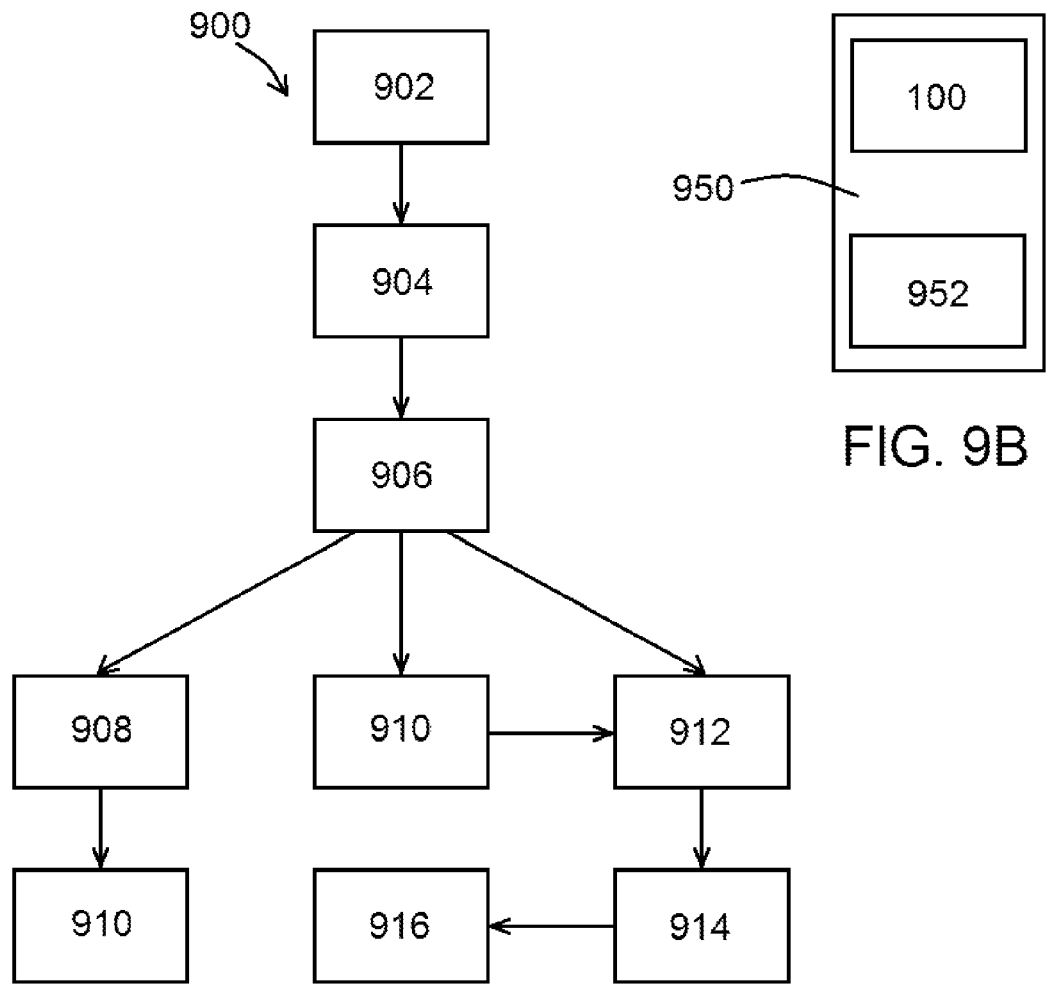
FIG. 9A shows steps of a method of determining whether a patient is suitable for a valve procedure, according to at least one exemplary embodiment of the present disclosure.
FIG. 9B shows a block diagram of a subsystem, according to at least one exemplary embodiment of the present disclosure.

In at least one embodiment of a method 900 of the present disclosure, and as shown in FIG. 9A, method 900 further comprises the step of incorporating data indicative of at least one valve into the digital model 1700 (an exemplary valve data incorporation step 910). Step 910 may be performed by incorporating native valve data or prosthetic valve data therein. Upon performance of step 910, in at least one embodiment, determination step 908 can be performed based at least in part on information including the patient venous data and the data indicative of at least one valve and/or patient venous data indicative of flow and shear stress. Further and in at least one embodiment, an ultimate determination can be made based upon a comparison of the patient venous data indicative of flow and shear stress to at least one threshold.

An exemplary method 900, as shown in FIG. 9A, may comprise the step of testing one or more virtual valve device configurations in at least one simulation using the digital model 1700 prepared in digital model preparation step 906 (an exemplary valve testing step 912). In at least one embodiment, the device configurations can be incorporated into the digital model 1700 such as by valve data incorporation step 910 referenced above. Valve testing step 912, as shown in FIG. 9A, may be performed after digital model preparation step 906 and optionally after valve data incorporation step 910, and involves performing at least one simulation using the digital model 1700. Determination step 908 and valve testing step 912 may be generally referred to herein as a test purpose.

Valve testing step 912, in various embodiments, may be performed to determine whether or not a virtual valve model is suitable for the patient that the digital model is based upon. For example, if a virtual valve model is tested in valve testing step 912 and it does not perform optimally, the virtual valve model can be modified and retested. In view of the same, an exemplary method 900 of the present disclosure may further comprise the steps of adjusting one or more virtual valve device configurations and retesting the adjusted one or more virtual valve device configurations (an exemplary adjustment step 914). Should steps 912 or 914 yield satisfactory results (indicative of a suitable virtual valve for the patient), a physical valve device based upon at least one of the adjusted virtual valve device configurations may be prepared (an exemplary valve preparation step 916), whereby the prepared valve (such as an endograft valve device 100 and/or valve system 700 of the present disclosure) may be positioned within the patient consistent with an exemplary method 800 of the present disclosure, for example.

Steps 912, 914, and/or 916 may be performed, as referenced above, to test, optimize, and produce a valve (such as a vein valve device) best suited for the modeled patient. The virtual testing, as referenced herein, allows for dozens, if not hundreds or thousands or more, of virtual devices to be tested, saving significant time and money over traditional physical valve manufacture and testing. In addition, such a method, as referenced above, is patient-specific, allowing for an optimized valve device, specifically tailored for the patient in need of the valve procedure (such as a valve replacement or valve insertion where no valve is present), resulting in optimal patient treatment. Such valve optimization (by way of performing steps 912 and/or 914) may be done to change one or more parameters, such as valve length, width, wall thickness, leaflet size, leaflet configuration, leaflet number(s), materials, curvatures, and/or a combination of the foregoing, for example, to optimize a valve for that particular patient. Such an optimized valve (ultimately produced in step 916, for example), may have one or more of the desired hemodynamic, mechanical, and/or functional properties sufficient for that particular patient's needs. For example, such an optimized valve may have two or more leaflets instead of one leaflet, and may be optimized so that a minimum amount of energy (or a reduced amount of energy) is needed to open and/or close the valve. Other valve configurations may be preferred based upon a different patient digital model 1700.

In various embodiments, determination step 908 is based at least in part on the patient venous data and the data indicative of at least one valve. In other embodiments, determination step 908 is based upon at least patient venous data indicative of flow and shear stress, and wherein an ultimate determination is based upon a comparison of the patient venous data indicative of flow and shear stress to at least one threshold.

Such a tailored approach defines the range of in vivo performance of the valve in a patient-specific mechanical environment. Although there are factors beyond mechanics that can be considered, a mechanical approach, and the data emanating therefrom, allows a practitioner to potentially identify non-mechanical factors. For example, if the valve fails in a percentage of the patients that satisfy mechanically-based inclusion criteria, then additional, non-mechanical biomarkers may be identified (such as blood chemistry, risk factors, co-morbidities, etc.). This data will then form the basis of a systematic and rigorous approach to embracing this complex patient population.

The third pillar, namely that no valve can function long-term in the absence of flow (and more specifically shear stress, is addressed as follows.

Venous Return Assist Device

Transcatheter aortic valve implantation (TAVI) has been successful, in large part, because the aortic valve prosthesis is coupled with the heart, namely that the heart pump ensures sufficient flow through the prosthetic. However, this is limited to aortic valves, and does not apply to venous valves, as the heart pump cannot ensure sufficient flow through a venous valve.

No valve can function without flow. The disclosure of the present application includes methods to generate venous blood flow (propulsion) through various assist devices (compression) and suction (release) within the vein, such as within the abdominal vena cavae. As discussed in further detail herein, said devices and methods can be used with our without valve implants, as if a native valve is functional, said devices and methods can be used to facilitate blood flow therethrough.

Under physiologic conditions, the peripheral pump (skeletal muscle), as well as the respiratory and abdominal phasic pressures, work in conjunction with the compliant veins to assist venous return in the presence of valves. Unfortunately, in patients of interest, venous hypertension-induced remodeling, thrombosis or fibrosis reduces the compliance of the veins (thicker and stiffer) and compromises the normal venous assist mechanisms. In such patients, an active assist mechanism for venous return is needed.

Figure 10A:
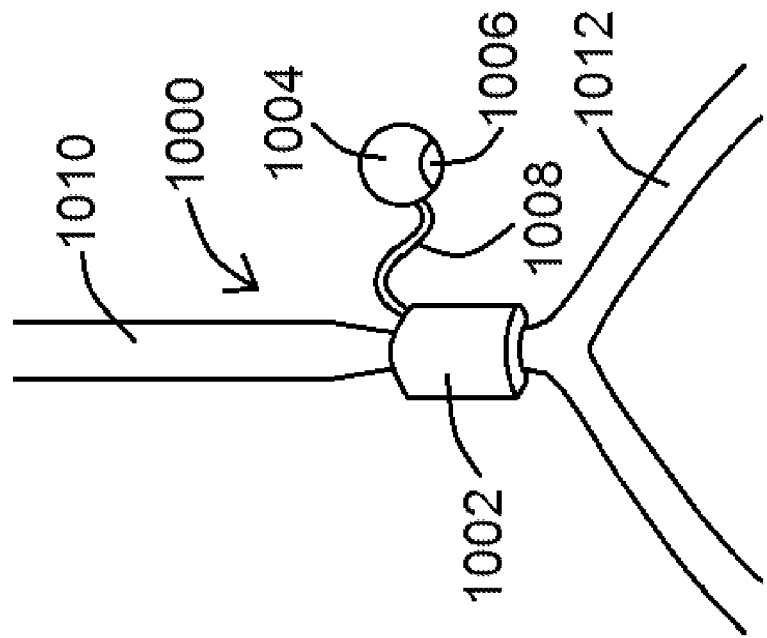
FIG. 10A shows an external assist device positioned around a blood vessel, according to at least one exemplary embodiment of the present disclosure.
Figure 10B:
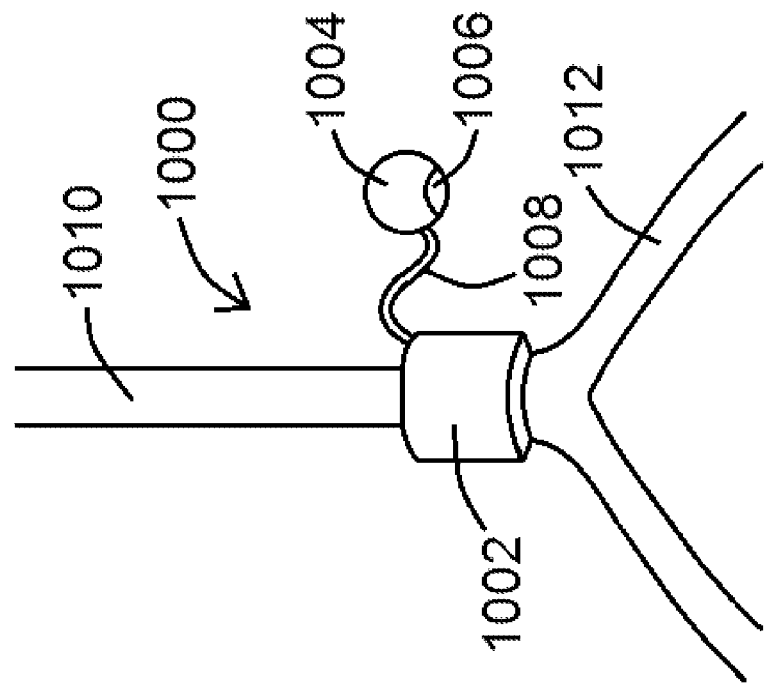
FIG. 10B shows an external assist device positioned around and constricting a blood vessel, according to at least one exemplary embodiment of the present disclosure.

The present disclosure includes disclosure of an exemplary external assist device operable to impose a force directly on the external surface of the vein to overcome the increased stiffness of the vein. As shown in FIGS. 10A and 10B, an exemplary assist device 1000 of the present disclosure comprises a cuff 1002 configured to fit around a blood vessel and further configured to periodically compress the blood vessel. Devices 1000, in various embodiments, are operably by way of a power source 1004 operably coupled to cuff 1002, so that power from power source 1004 can control the compression and relaxation of cuff 1002. Power source 1004 may comprise, for example, an implanted battery, which may be rechargeable, and/or a power source 1004 positioned external to the patient's body. A processor 1006, operably coupled to power source 1004, is configured to control the rates of compression and relaxation of cuff 1002. As referenced herein, a processor 1006 may comprise a processor or a processor in operable communication with a storage device, whereby the processor can operate based on data stored in storage device and/or operate to generate data for storage within storage device. In at least one embodiment, processor 1006 is configured so that the compression rate and the relaxation rate can be changed to a different compression rate and a different relaxation rate. As shown in FIGS. 10A and 10B, an optional connector 1008, such as a wire, may be used to connect power source 1004 to cuff 1002, wherein connector 1008 configured to allow power from power source 1004 to be transmitted therethrough to cuff 1002.

FIG. 10A shows an exemplary assist device 1000 of the present disclosure positioned around an abdominal vena cava (an exemplary blood vessel 1010). Blood flowing from an iliac vein 1012, for example, would flow through the vena cava and be assisted using an exemplary assist device 1000. Device 1000 is shown in FIG. 10A as positioned around, but not compressing, the vena cava, while an exemplary device 1000 of the present disclosure is shown in FIG. 10B positioned around and compressing the vena cava. Devices 1000 of the present disclosure are not limited to being configured around a vena cava, as said devices 1000 may be configured to fit around any number of blood vessels within a mammalian body.

In at least one embodiment of a device 1000 of the present disclosure, when device 1000 is positioned around a blood vessel at a first location, operation of processor 1006 causes cuff 1002 to alternately compress the blood vessel and relax compression of the blood vessel. Processor 1006 controls a compression rate and a relaxation rate (which may be the same or different), whereby relaxation at the relaxation rate causes blood to move through the blood vessel at the first location. In at least one embodiment, the compression rate is slower than the relaxation rate, as a relatively faster relaxation rate allows the blood vessel to open quicker and effectively pull blood through the blood vessel at the first location. A power source 1004 operably coupled to cuff 1002 would be configured to provide power to cuff 1002 and/or processor 1006 to facilitate compression and relaxation of cuff 1002.

In various embodiments of devices 1000, processor 1006 is configured so that the compression rate and the relaxation rate can be changed to a different compression rate and a different relaxation rate. In at least one embodiment, when device 1000 is positioned distal to a blood vessel valve (such as an endograft valve device 100 as referenced herein), operation of device 1000 causes blood to flow through the vessel valve toward device 1000. The blood vessel valve may be a native valve or a prosthetic valve, as devices 1000 of the present disclosure are configured to facilitate blood flow through both types of valves.

In at least one embodiment, when device 1000 is positioned around the blood vessel at a first location, the blood flows through the blood vessel at the first location a first rate without operation of device 100, and the blood flows through the blood vessel at the first location at a second rate during operation of device 1000, wherein the second rate is faster than the first rate. Furthermore, and in various embodiments, when device 1000 is positioned around the blood vessel at a first location, the blood flows through the blood vessel at the first location a first rate range without operation of device 100, and the blood flows through the blood vessel at the first location at a second rate range during operation of device 1000, wherein the second rate range has a faster top rate than the first rate range. The two ranges include the slowest relative flow rate, the fastest relative flow rate, and potentially various flow rates in between.

Figure 11:
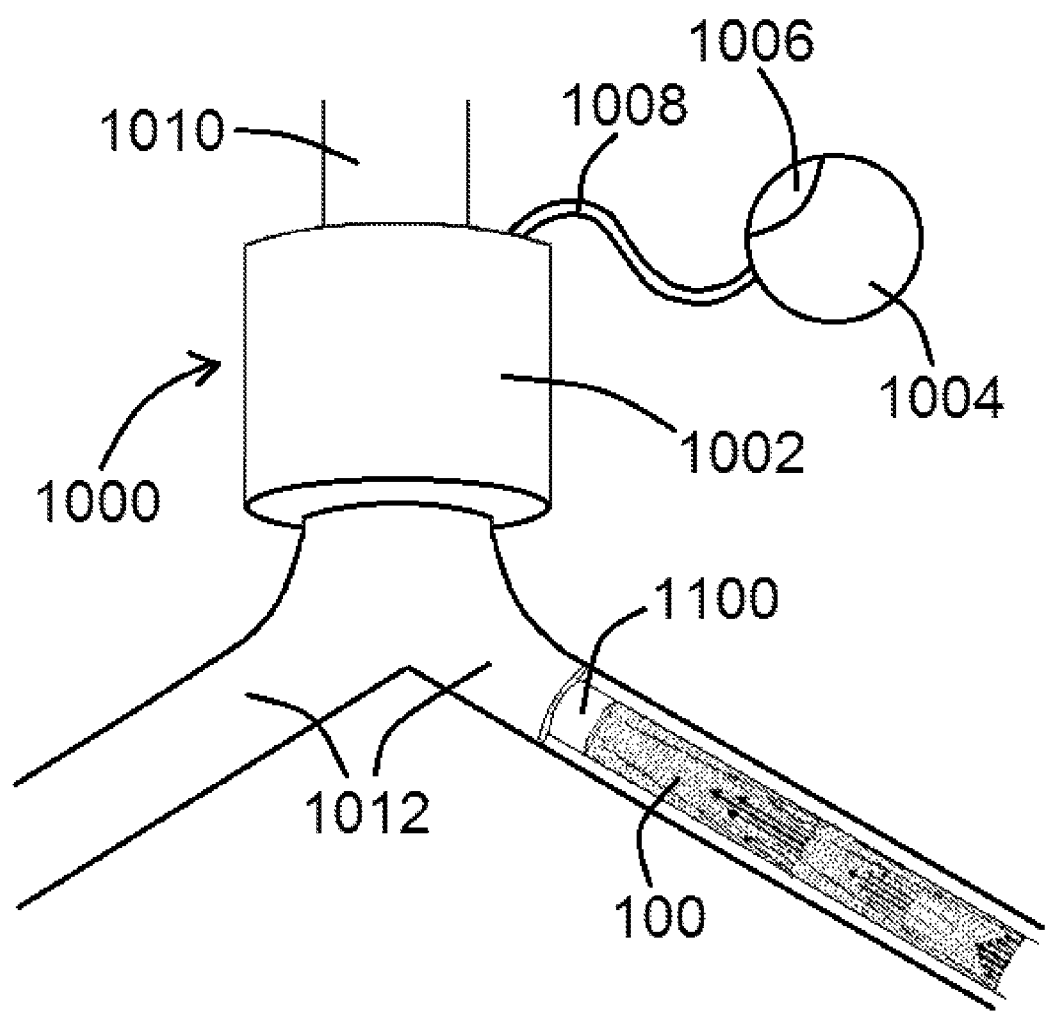
FIG. 11 shows an external assist device positioned around a blood vessel and an endograft valve device positioned within a vessel, according to at least one exemplary embodiment of the present disclosure.

FIG. 11 shows a larger view of an exemplary device 1000 of the present disclosure positioned around a blood vessel 1010, and further shows an exemplary endograft valve device 100 positioned within a lumen 1100 of a blood vessel 1012 proximal to where device 1000 is positioned. As shown in FIG. 11, device 1000 is positioned about a vena cava, while device 100 is positioned within an iliac vein 1012 proximal to device 1000. Operation of device 1000, when positioned as shown in FIG. 11 relative to device 100, causes blood to be pulled through vessel 1010 at the location of device 1000, and therefore causes blood to be pulled through device 100 proximal to device 1000.

Use of various devices 1000 of the present disclosure provides an assist mechanism where compression of the vein propels the blood flow (in the presence of functional valve, either native or prosthetic) towards the heart. A quick release of the compression of device 1000 can create the effect of suction to "pull" the blood from the periphery again in the direction of the heart. Other devices, such as the devices disclosed within US2010/0179376 of Kassab and Navia, may also be configured to fit around a vessel (such as a vein, as referenced herein) and further configured to compress and release the blood vessel so to, for example, facilitate blood flow through a vein when the device is positioned around the vein. Said devices are hereby incorporated into the present disclosure by reference.

Figure 12:
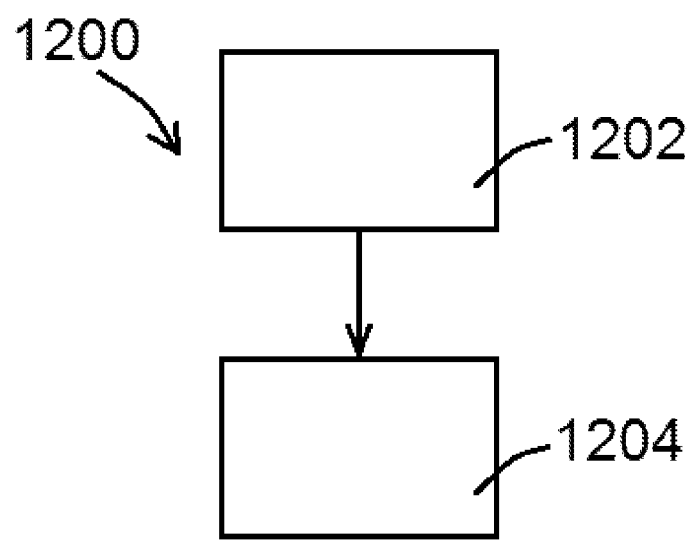
FIG. 12 shows steps of a method of facilitating blood flow through a blood vessel, according to at least one exemplary embodiment of the present disclosure.

The present disclosure also includes disclosure of a method of facilitating blood flow through a blood vessel. In at least one embodiment of a method 1200 of the present disclosure, as shown by the method steps in FIG. 12, the method comprises the steps of positioning an exemplary external assist device 1000 of the present disclosure around a blood vessel (an exemplary positioning step 1202), and operating external assist device 1000 to alternatively compress the blood vessel and relax compression of the blood vessel (an exemplary operating step 1204), wherein relaxation of compression causes blood to flow through the blood vessel. Relaxation of compression of device 1000, as referenced herein, causes blood to flow through the blood vessel at a faster rate than a native blood flow rate. In at least one embodiment of method 1200 of the present disclosure, operating step 1204 comprises operating external assist device 1000 to alternative compress the blood vessel at a first rate and to relax compression of the blood vessel at a second rate, wherein the second rate is faster than the first rate.

Various devices 1000 of the present disclosure may be delivered minimally invasively through a laparoscopic approach to induce a pumping action to propel the flow forward in opposition to gravity.

While various embodiments of devices and methods for assisting valve function, replacing venous valves, and predicting valve treatment successes been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An endograft valve device, comprising:
   an endograft body configured for expansion within a luminal organ, the endograft body comprising:
   a first portion having a proximal end defining a proximal end aperture and a distal end defining a distal end aperture, the first portion internally tapered inward from the proximal end to the distal end when the endograft body is expanded and configured to increase a velocity of fluid flowing therethrough;
   a second portion having a second portion proximal end defining a second portion proximal end aperture and a second portion distal end defining a second portion distal end aperture, wherein the distal end of the first portion is adjacent to the second portion proximal end and wherein the second portion is internally tapered inward from the second portion proximal end to the second portion distal end; and
   a valve portion positioned at or near the second portion proximal end or the distal end of the first portion, the valve portion configured to receive the fluid flowing through the distal end aperture of the first portion;
   wherein the endograft valve device is sized and shaped to fit within the luminal organ, the size and shape based upon data obtained relative to a flow velocity of blood within a vein of a patient.

2. An endograft valve device, comprising:
   an endograft body configured for expansion within a luminal organ, the endograft body comprising:
   a first portion having a proximal end defining a proximal end aperture and a distal end defining a distal end aperture, the first portion internally tapered inward from the proximal end to the distal end when the endograft body is expanded and configured to increase a velocity of fluid flowing therethrough;
   a second portion having a second portion proximal end defining a second portion proximal end aperture and a second portion distal end defining a second portion distal end aperture, wherein the distal end of the first portion is adjacent to the second portion proximal end and wherein the second portion is internally tapered inward from the second portion proximal end to the second portion distal end; and
   a valve portion positioned at or near the second portion proximal end or the distal end of the first portion, the valve portion configured to receive the fluid flowing through the distal end aperture of the first portion;
   wherein the endograft valve device is configured based upon a digital model of a luminal organ of a patient;
   wherein the digital model incorporates a vessel geometry input indicative of data obtained relative to a patient's venous geometry at a first location; and
   wherein the digital model further incorporates a flow velocity input indicative of data obtained relative to a flow velocity of blood within the vein of the patient.

3. The endograft valve device of claim 2, wherein the digital model is configured to generate at least one model output based upon at least the vessel geometry input and the flow velocity input.

4. The endograft valve device of claim 3, wherein the at least one model output indicates whether or not the patient is suitable for a valve procedure.

5. The endograft valve device of claim 3, wherein the at least one model output indicates that the patient is suitable for a valve procedure based upon at least the vessel geometry input, the flow velocity input, and the valve input, as compared to at least one threshold parameter.

6. The endograft valve device of claim 5, wherein the at least one threshold parameter is selected from the group consisting of a minimum vessel diameter, a vessel diameter range, a minimum flow velocity, a flow velocity range, a minimum vessel cross-sectional area, a vessel cross-sectional area range, a minimum wall stress parameter, a maximum wall stress parameter, a minimum wall shear stress parameter, a maximum wall shear stress parameter, a minimum gradient of wall shear stress parameter, a maximum gradient of wall shear stress parameter, a minimum oscillatory shear index parameter, a maximum oscillatory shear index parameter, and a leaflet closure parameter.

7. The endograft valve device of claim 5, wherein the at least one threshold parameter is selected from the group consisting of a vessel diameter larger than or approximately 8 mm, a cross-sectional area larger than or approximately 0.5 cm$^2$, a flow velocity greater than or approximately 30 ml/min, and a wall shear stress greater than or approximately 5 dynes/cm$^2$ and less than or approximately 10 dynes/cm$^2$.

8. The endograft valve device of claim 3, wherein the at least one model output indicates that the patient is not suitable for a valve procedure based upon fibrosis within the patient's vessel geometry.

9. The endograft valve device of claim 3, wherein the at least one model output indicates that the patient is not suitable for a valve procedure based upon at least the vessel geometry input, the flow velocity input, and the valve input, as compared to at least one threshold parameter.

10. The endograft valve device of claim 9, wherein the at least one threshold parameter is selected from the group consisting of a vessel diameter less than or approximately 8 mm, a cross-sectional area less than or approximately 0.5 cm$^2$, a flow velocity less than or approximately 30 ml/min, a flow velocity greater than or approximately 150 ml/min, a wall shear stress less than or approximately 5 dynes/cm$^2$, and a wall shear stress greater than or approximately 10 dynes/cm$^2$.

11. The endograft valve device of claim 2, wherein the digital model further incorporates a valve input indicative of at least one digital valve device.

12. The endograft valve device of claim 11, wherein the digital model is configured to generate at least one model output based upon at least the vessel geometry input, the flow velocity input, and the valve input.

13. The endograft valve device of claim 12, wherein the at least one model output indicates whether or not the patient is suitable for a valve procedure based on one or more characteristics of the valve input.

14. The endograft valve device of claim 12, wherein the one or more characteristics of the valve input is/are selected from the group consisting of a wall stress characteristic, a wall shear stress characteristic, a gradient of wall shear stress characteristic, an oscillatory shear index characteristic, and a leaflet characteristic.

15. The endograft valve device of claim 12, wherein the at least one digital valve device includes a configuration of the endograft valve device, and wherein the endograft valve device is selected for implantation into the patient based upon the model output.

16. The endograft valve device of claim 11, wherein the digital model comprises a processor operably coupled to a storage medium, the processor operable to generate the at least one model output, and the storage medium configured to store data relating to the vessel geometry input, the flow velocity input, the valve input, and the at least one model output.

17. The endograft valve device of claim 11, wherein the digital model further incorporates a thrombosis input indicative of a level of thrombosis within the vessel geometry.

18. The endograft valve device of claim 17, wherein the digital model is configured to generate at least one model output based upon at least the vessel geometry input, the flow velocity input, the valve input, and the thrombosis input.

19. The endograft valve device of claim 17, wherein the digital model further incorporates a rheology input indicative of a blood rheology property.

20. An endograft valve device, comprising:

an endograft body configured for expansion within a luminal organ, the endograft body comprising:

a first portion having a proximal end defining a proximal end aperture and a distal end defining a distal end aperture, the first portion internally tapered inward from the proximal end to the distal end when the endograft body is expanded and configured to increase a velocity of fluid flowing therethrough;

a second portion having a second portion proximal end defining a second portion proximal end aperture and a second portion distal end defining a second portion distal end aperture, wherein the distal end of the first portion is adjacent to the second portion proximal end and wherein the second portion is internally tapered inward from the second portion proximal end to the second portion distal end; and a valve portion positioned at or near the second portion proximal end or the distal end of the first portion, the valve portion configured to receive the fluid flowing through the distal end aperture of the first portion;

wherein the endograft valve device comprises a component of a valve system, the valve system further comprising a cuff configured to fit around a blood vessel and further configured to periodically compress the blood vessel;

wherein the endograft valve device is sized and shaped to fit within the luminal organ, the size and shape based upon data obtained relative to a flow velocity of blood within a vein of a patient;

wherein the valve system further comprises a processor operably coupled to the cuff, the processor configured to control a compression rate and a relaxation rate;

wherein when the cuff is positioned around the blood vessel at a second location, operation of the processor causes the cuff to compress the blood vessel and relax compression of the blood vessel, whereby relaxation at the relaxation rate increases a rate of blood flow through the blood vessel at the second location; and wherein when the endograft valve device is positioned within the blood vessel at a first location and wherein when the cuff is positioned around the blood vessel at the second location, operation of the cuff increases the rate of blood flow through the blood vessel at the first location and the second location.

* * * * *